US011268103B2

(12) United States Patent
Castiglioni et al.

(10) Patent No.: US 11,268,103 B2
(45) Date of Patent: Mar. 8, 2022

(54) TRANSGENIC PLANTS WITH ENHANCED TRAITS

(71) Applicant: Monsanto Technology LLC, St. Louis, MO (US)

(72) Inventors: Paolo Castiglioni, Davis, CA (US); Jaishree M. Chittoor-Vijayanath, Wildwood, MO (US); Barry S. Goldman, St. Louis, MO (US); Robert J. Meister, St. Peters, MO (US); Monnanda S. Rajani, Chesterfield, MO (US); G. Ramamohan, Bangalore (IN); Naveen Silvester, Bangalore (IN); Tyamagondlu V. Venkatesh, St. Louis, MO (US); Jingrui Wu, Johnston, IA (US); Xiaoyun Wu, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 315 days.

(21) Appl. No.: 14/395,697

(22) PCT Filed: Mar. 6, 2013

(86) PCT No.: PCT/US2013/029231
§ 371 (c)(1),
(2) Date: Oct. 20, 2014

(87) PCT Pub. No.: WO2013/158228
PCT Pub. Date: Oct. 24, 2013

(65) Prior Publication Data
US 2015/0096069 A1   Apr. 2, 2015

Related U.S. Application Data

(60) Provisional application No. 61/635,946, filed on Apr. 20, 2012.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8201* (2013.01); *C12N 15/825* (2013.01); *C12N 15/8242* (2013.01); *C12N 15/8271* (2013.01); *C12N 15/8273* (2013.01); *Y02A 40/146* (2018.01)

(58) Field of Classification Search
None
See application file for complete search history.

(56) References Cited

U.S. PATENT DOCUMENTS

| 7,176,351 | B2* | 2/2007 | Kisaka | ................ C08B 30/048 435/320.1 |
| 7,820,882 | B2* | 10/2010 | Dubcovsky | .......... C07K 14/415 435/320.1 |
| 8,378,173 | B2* | 2/2013 | Hu | ..................... C12N 15/8273 435/252.3 |
| 2009/0276918 | A1* | 11/2009 | Choi | ................ C12N 15/8261 800/278 |
| 2010/0186108 | A1 | 7/2010 | Hu et al. | |
| 2011/0162107 | A1 | 6/2011 | Inze et al. | |
| 2015/0150158 | A1* | 5/2015 | Reuzeau | ............ C12N 15/8261 800/287 |

OTHER PUBLICATIONS

Hu et al. Overexpressing a NAM, ATAF, and CUC (NAC) transcription factor enhances drought resistance and salt tolerance in rice. Proc Natl Acad Sci U S A. Aug. 29, 2006;103(35):12987-92. Epub Aug. 21, 2006.*
Yokotani et al. Tolerance to various environmental stresses conferred by the salt-responsive rice gene ONAC063 in transgenic Arabidopsis. Planta (2009) 229:1065-1075.*
GenBank Accession No. GU014814, Oryza sativa Indica Group cultivar N22 stress-induced transcription factor NAC1 (Snac1) mRNA, complete cds. Oct. 20, 2009. (Year: 2009).*

* cited by examiner

*Primary Examiner* — Cynthia E Collins
(74) *Attorney, Agent, or Firm* — Morrison & Foerster LLP

(57) ABSTRACT

This disclosure provides transgenic plants having enhanced traits such as increased yield, enhanced nitrogen use efficiency and enhanced drought tolerance; propagules, progeny and field crops of such transgenic plants; and methods of making and using such transgenic plants. This disclosure also provides methods of producing hybrid seed from such transgenic plants, growing such seed and selecting progeny plants with enhanced traits. Also disclosed are transgenic plants with altered phenotypes which are useful for screening and selecting transgenic events for the desired enhanced trait.

10 Claims, No Drawings
Specification includes a Sequence Listing.

TRANSGENIC PLANTS WITH ENHANCED TRAITS

REFERENCE TO RELATED APPLICATIONS

This application is National Stage of International Application No. PCT/US2013/029231 filed 06 Mar. 2013, which claims priority to U.S. Provisional Application No. 61/635,946 filed on 20 Apr. 2012, which are incorporated herein by reference.

INCORPORATION OF SEQUENCE LISTING

The Sequence Listing accompanying this application is contained within the computer readable file "38-21(58904)US0001_SeqListing.txt" submitted electronically and contemporaneously with the filing of this application through the USPTO EFS-Web. The file is 63 KB (measured in MS-Windows), was created on 17 Oct. 2014, and is incorporated herein by reference.

FIELD OF THE INVENTION

Disclosed herein are plants having enhanced traits such as increased yield, increased nitrogen use efficiency and increased water use efficiency; propagules, progenies and field crops of such plants; and methods of making and using such plants. Also disclosed are methods of producing seed from such plants, growing such seed and/or selecting progeny plants with enhanced traits.

SUMMARY OF THE INVENTION

An aspect of this disclosure provides a plant comprising a recombinant DNA molecule comprising a polynucleotide encoding a polypeptide, wherein the nucleotide sequence of the polynucleotide is selected from the group consisting of: a) a nucleotide sequence set forth as SEQ ID NO: 1, 3, 5, 7, 9, 11, 13, 15, 17, or 19; b) a nucleotide sequence encoding a protein having the amino acid sequence of SEQ ID NO: 2, 4, 6, 8, 10, 12, 14, 16, 18, or 20-29; c) a nucleotide sequence with at least 90%, at least 91%, at least 92%, at least 93%, at least 94%, at least 95%, at least 96%, at least 97%, at least 98%, at least 99% identity to SEQ ID NO: 1, 3, 5, 7, 9, 11, 13, 15, 17, or 19; and d) a nucleotide sequence encoding a protein with at least 90%, at least 91%, at least 92%, at least 93%, at least 94%, at least 95%, at least 96%, at least 97%, at least 98%, at least 99% identity to SEQ ID NO: 2, 4, 6, 8, 10, 12, 14, 16, 18, or 20-29; wherein said plant has enhanced trait as compared to a control plant, and wherein said enhanced trait is selected from the group consisting of increased yield, increased nitrogen use efficiency, and increased water use efficiency.

Another aspect of this disclosure provides a plant comprising a recombinant DNA molecule of the disclosure, wherein said plant is a monocot plant or is a member of the family Poaceae, wheat plant, maize plant, sweet corn plant, rice plant, wild rice plant, barley plant, rye, millet plant, sorghum plant, sugar cane plant, turfgrass plant, bamboo plant, oat plant, brome-grass plant, *Miscanthus* plant, pampas grass plant, switchgrass (*Panicum*) plant, and/or teosinte plant, or is a member of the family Alliaceae, onion plant, leek plant, garlic plant; or wherein the plant is a dicot plant or is a member of the family Amaranthaceae, spinach plant, *quinoa* plant, a member of the family Anacardiaceae, mango plant, a member of the family Asteraceae, sunflower plant, endive plant, lettuce plant, artichoke plant, a member of the family Brassicaceae, *Arabidopsis thaliana* plant, rape plant, oilseed rape plant, broccoli plant, Brussels sprouts plant, cabbage plant, canola plant, cauliflower plant, kohlrabi plant, turnip plant, radish plant, a member of the family Bromeliaceae, pineapple plant, a member of the family Caricaceae, *papaya* plant, a member of the family Chenopodiaceae, beet plant, a member of the family Curcurbitaceae, melon plant, cantaloupe plant, squash plant, watermelon plant, honeydew plant, cucumber plant, pumpkin plant, a member of the family Dioscoreaceae, yam plant, a member of the family Ericaceae, blueberry plant, a member of the family Euphorbiaceae, cassava plant, a member of the family Fabaceae, alfalfa plant, clover plant, peanut plant, a member of the family Grossulariaceae, currant plant, a member of the family Juglandaceae, walnut plant, a member of the family Lamiaceae, mint plant, a member of the family Lauraceae, avocado plant, a member of the family Leguminosae, soybean plant, bean plant, pea plant, a member of the family Malvaceae, cotton plant, a member of the family Marantaceae, arrowroot plant, a member of the family Myrtaceae, guava plant, *eucalyptus* plant, a member of the family Rosaceae, peach plant, apple plant, cherry plant, plum plant, pear plant, prune plant, blackberry plant, raspberry plant, strawberry plant, a member of the family Rubiaceae, coffee plant, a member of the family Rutaceae, citrus plant, orange plant, lemon plant, grapefruit plant, tangerine plant, a member of the family Salicaceae, poplar plant, willow plant, a member of the family Solanaceae, potato plant, sweet potato plant, tomato plant, *Capsicum* plant, tobacco plant, tomatillo plant, eggplant plant, *Atropa belladona* plant, *Datura stramonium* plant, a member of the family Vitaceae, grape plant, a member of the family Umbelliferae, carrot plant, or a member of the family Musaceae, banana plant; or wherein the plant is a member of the family Pinaceae, cedar plant, fir plant, hemlock plant, larch plant, pine plant, or spruce plant.

Another aspect of this disclosure provides a plant comprising a recombinant DNA molecule of the disclosure, wherein the recombinant DNA molecule further comprises a promoter that is operably linked to the polynucleotide encoding a polypeptide, wherein said promoter is selected from the group consisting of a constitutive, inducible, tissue specific, diurnally regulated, tissue enhanced, and cell specific promoter.

Another aspect of this disclosure provides a plant comprising a recombinant DNA molecule of the disclosure, wherein said plant is a progeny, propagule, or field crop. Such field crop is selected from the group consisting of corn, soybean, cotton, canola, rice, barley, oat, wheat, turf grass, alfalfa, sugar beet, sunflower, *quinoa* and sugar cane.

Another aspect of this disclosure provides a plant comprising a recombinant DNA molecule of the disclosure, wherein said plant is a progeny, propagule, or field crop. Such propagule is selected from the group consisting of a cell, pollen, ovule, flower, embryo, leaf, root, stem, shoot, meristem, grain and seed.

Another aspect of this disclosure provides a method of producing a plant comprising: introducing into a plant cell a recombinant DNA comprising a polynucleotide encoding a polypeptide, wherein the nucleotide sequence of the polynucleotide is selected from the group consisting of: a) a nucleotide sequence set forth as SEQ ID NO: 1, 3, 5, 7, 9, 11, 13, 15, 17, or 19; b) a nucleotide sequence encoding a protein having the amino acid sequence of SEQ ID NO: 2, 4, 6, 8, 10, 12, 14, 16, 18, or 20-29; c) a nucleotide sequence with at least 90%, at least 91%, at least 92%, at least 93%, at least 94%, at least 95%, at least 96%, at least 97%, at least 98%, at least 99% identity to SEQ ID NO: 1, 3, 5, 7, 9, 11, 13, 15, 17, or 19; and d) a nucleotide sequence encoding a protein with at least 90%, at least 91%, at least 92%, at least 93%, at least 94%, at least 95%, at least 96%, at least 97%, at least 98%, at least 99% identity to SEQ ID NO: 2, 4, 6, 8, 10, 12, 14, 16, 18, or 20-29; and growing a plant from said plant cell.

Another aspect of this disclosure provides a method of producing a plant comprising: introducing into a plant cell a recombinant DNA molecule of the disclosure; growing a plant from said plant cell; and selecting a plant with an enhanced trait selected from increased yield, increased nitrogen use efficiency, and increased water use efficiency as compared to a control plant.

Another aspect of this disclosure provides a method of increasing yield, increasing nitrogen use efficiency, or increasing water use efficiency in a plant comprising: producing a plant comprising a recombinant DNA of the disclosure wherein said plant has an enhanced trait selected from the group consisting of increased yield, increased nitrogen use efficiency, and increased water use efficiency as compared to a control plant; crossing said plant with itself, a second plant from the same plant line, a wild type plant, or a second plant from a different line of plants to produce a seed; growing said seed to produce a plurality of progeny plants, and selecting a progeny plant with increased yield, increased nitrogen use efficiency, or increased water use efficiency.

Another aspect of this disclosure provides a plant comprising a recombinant DNA molecule comprising a polynucleotide encoding a polypeptide, wherein the nucleotide sequence of the polynucleotide is selected from the group consisting of: a) a nucleotide sequence set forth as SEQ ID NO: 1, 3, 5, 7, 9, 11, 13, 15, 17, or 19; b) a nucleotide sequence encoding a protein having the amino acid sequence of SEQ ID NO: 2, 4, 6, 8, 10, 12, 14, 16, 18, or 20-29; c) a nucleotide sequence with at least 90%, at least 91%, at least 92%, at least 93%, at least 94%, at least 95%, at least 96%, at least 97%, at least 98%, at least 99% identity to SEQ ID NO: 1, 3, 5, 7, 9, 11, 13, 15, 17, or 19; and d) a nucleotide sequence encoding a protein with at least 90%, at least 91%, at least 92%, at least 93%, at least 94%, at least 95%, at least 96%, at least 97%, at least 98%, at least 99% identity to SEQ ID NO: 2, 4, 6, 8, 10, 12, 14, 16, 18, or 20-29; wherein said plant has at least one phenotype selected from the group consisting of anthocyanin, biomass, canopy area, chlorophyll score, plant height, water applied, water content and water use efficiency that is altered for said plant as compared to a control plant.

DETAILED DESCRIPTION OF THE INVENTION

In the attached sequence listing:

SEQ ID NOs: 1, 3, 5, 7, 9, 11, 13, 15, 17, and 19 are nucleotide sequences of the coding strand of the DNA molecules used in the recombinant DNA imparting an enhanced trait in plants, each represents a coding sequence for a protein.

SEQ ID NOs: 2, 4, 6, 8, 10, 12, 14, 16, 18, and 20 are amino acid sequences of the cognate proteins of the DNA molecules with nucleotide sequences 1, 3, 5, 7, 9, 11, 13, 15, 17, and 19.

SEQ ID NOs: 21-29 are amino acid sequences of homologous proteins.

As used herein a "plant" includes whole plant, transgenic plant, meritem, shoot organ/structure (for example, leaf, stem and tuber), root, flower and floral organ/structure (for example, bract, sepal, petal, stamen, carpel, anther and ovule), seed (including embryo, endosperm, and seed coat) and fruit (the mature ovary), plant tissue (for example, vascular tissue, ground tissue, and the like) and cell (for example, guard cell, egg cell, pollen, mesophyll cell, and the like), and progeny of same. The classes of plants that can be used in the disclosed methods are generally as broad as the classes of higher and lower plants amenable to transformation and breeding techniques, including angiosperms (monocotyledonous and dicotyledonous plants), gymnosperms, ferns, horsetails, psilophytes, lycophytes, bryophytes, and multicellular *algae*.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transgenic plant.

As used herein a "control plant" means a plant that does not contain the recombinant DNA that imparts an enhanced trait. A control plant is used to identify and select a transgenic plant that has an enhanced trait. A suitable control plant can be a non-transgenic plant of the parental line used to generate a transgenic plant, for example, a wild type plant devoid of a recombinant DNA. A suitable control plant can also be a transgenic plant that contains the recombinant DNA that imparts other traits, for example, a transgenic plant having enhanced herbicide tolerance. A suitable control plant can in some cases be a progeny of a hemizygous transgenic plant line that does not contain the recombinant DNA, known as a negative segregant, or a negative isoline.

As used herein a "transgenic plant cell" means a plant cell that is transformed with stably-integrated, recombinant DNA, for example, by *Agrobacterium*-mediated transformation or by bombardment using microparticles coated with recombinant DNA or by other means. A plant cell of this disclosure can be an originally-transformed plant cell that exists as a microorganism or as a progeny plant cell that is regenerated into differentiated tissue, for example, into a transgenic plant with stably-integrated, recombinant DNA, or seed or pollen derived from a progeny transgenic plant.

As used herein a "propagule" includes all products of meiosis and mitosis, including but not limited to, plant, seed and part of a plant able to propagate a new plant. Propagules include whole plants, cells, pollen, ovules, flowers, embryos, leaves, roots, stems, shoots, meristems, grains or seeds, or any plant part that is capable of growing into an entire plant. Propagule also includes graft where one portion of a plant is grafted to another portion of a different plant (even one of a different species) to create a living organism. Propagule also includes all plants and seeds produced by cloning or by bringing together meiotic products, or allowing meiotic products to come together to form an embryo or a fertilized egg (naturally or with human intervention).

As used herein a "progeny" includes any plant, seed, plant cell, and/or regenerable plant part comprising a recombinant DNA of the present disclosure derived from an ancestor plant. A progeny can be homozygous or heterozygous for the transgene. Progeny can be grown from seeds produced by a transgenic plant comprising a recombinant DNA of the present disclosure, and/or from seeds produced by a plant fertilized with pollen or ovule from a transgenic plant comprising a recombinant DNA of the present disclosure.

As used herein a "trait" is a physiological, morphological, biochemical, or physical characteristic of a plant or particular plant material or cell. In some instances, this characteristic is visible to the human eye, such as seed or plant size, or can be measured by biochemical techniques, such as detecting the protein, starch, certain metabolites, or oil content of seed or leaves, or by observation of a metabolic or physiological process, for example, by measuring tolerance to water deprivation or particular salt or sugar concentrations, or by the measurement of the expression level of a gene or genes, for example—by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

As used herein an "enhanced trait" means a characteristic of a transgenic plant as a result of stable integration and expression of a recombinant DNA in the transgenic plant. Such traits include, but are not limited to, an enhanced agronomic trait characterized by enhanced plant morphology, physiology, growth and development, yield, nutritional enhancement, disease or pest resistance, or environmental or chemical tolerance. In some specific aspects of this disclosure an enhanced trait is selected from the group consisting of drought tolerance, increased water use efficiency, cold tolerance, increased nitrogen use efficiency, increased yield, and altered phenotypes as shown in Tables 3-5. In another aspect of the disclosure the trait is increased yield under non-stress conditions or increased yield under environmental stress conditions. Stress conditions can include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, plant biomass, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Also used herein, the term "trait modification" encompasses altering the naturally occurring trait by producing a detectable difference in a characteristic in a plant comprising a recombinant DNA encoding a polypeptide of the present disclosure relative to a plant not comprising the recombinant DNA, such as a wild-type plant, or a negative segregant. In some cases, the trait modification can be evaluated quantitatively. For example, the trait modification can entail an increase or decrease, in an observed trait as compared to a control plant. It is known that there can be natural variations in the modified trait. Therefore, the trait modification observed entails a change of the normal distribution and magnitude of the trait in the plants as compared to a control plant.

Increased yield of a plant of the present disclosure can be measured in a number of ways, including test weight, seed number per plant, seed weight, seed number per unit area (for example, seeds, or weight of seeds, per acre), bushels per acre, tons per acre, or kilo per hectare. For example, corn yield can be measured as production of shelled corn kernels per unit of production area, for example in bushels per acre or metric tons per hectare. This is often also reported on a moisture adjusted basis, for example at 15.5 percent moisture. Increased yield can result from improved utilization of key biochemical compounds, such as nitrogen, phosphorous and carbohydrate, or from improved responses to environmental stresses, such as cold, heat, drought, salt, shade, high plant density, and attack by pests or pathogens. This disclosure can also be used to provide plants with improved growth and development, and ultimately increased yield, as the result of modified expression of plant growth regulators or modification of cell cycle or photosynthesis pathways. Also of interest is the generation of plants that demonstrate increased yield with respect to a seed component that may or may not correspond to an increase in overall plant yield.

The present disclosure relates to a plant with improved economically important characteristics, more specifically increased yield. More specifically the present disclosure relates to a plant comprising a polynucleotide of this disclosure that encodes a polypeptide, wherein the plant has increased yield as compared to a control plant. Many plants of this disclosure exhibited increased yield as compared to a control plant. In an embodiment, a plant of the present disclosure exhibited an improved trait that is a component of yield.

The present disclosure relates to a plant with improved economically important characteristics, more specifically increased yield. More specifically the present disclosure relates to a plant comprising a polynucleotide of this disclosure that encodes a polypeptide, wherein the plant has increased yield as compared to a control plant. Many plants of this disclosure exhibited increased yield as compared to a control plant. In an embodiment, a plant of the present disclosure exhibited an improved trait that is a component of yield.

Reference herein to an increase in yield-related traits can also be taken to mean an increase in biomass (weight) of one or more parts of a plant, which can include above ground and/or below ground (harvestable) plant parts. In particular, such harvestable parts are seeds, and performance of the methods of the disclosure results in plants with increased yield and in particular increased seed yield relative to the seed yield of suitable control plants. The term "yield" of a plant can relate to vegetative biomass (root and/or shoot biomass), to reproductive organs, and/or to propagules (such as seeds) of that plant.

In an embodiment, "alfalfa yield" can also be measured in forage yield, the amount of above ground biomass at harvest. Factors leading contributing to increased biomass include increased vegetative growth, branches, nodes and internodes, leaf area, and leaf area index.

In another embodiment, "canola yield" can also be measured in pod number, number of pods per plant, number of pods per node, number of internodes, incidence of pod shatter, seeds per silique, seed weight per silique, improved seed, oil, or protein composition.

Additionally, "corn or maize yield" can also be measured as production of shelled corn kernels per unit of production area, ears per acre, number of kernel rows per ear, weight per kernel, ear number, fresh or dry ear biomass (weight), kernel rows per ear and kernels per row.

In yet another embodiment, "cotton yield" can be measured as bolls per plant, size of bolls, fiber quality, seed cotton yield in g/plant, seed cotton yield in lb/acre, lint yield in lb/acre, and number of bales.

Specific embodiments for "rice yield" can also include panicles per hill, grain per hill, and filled grains per panicle.

Still further embodiment for "soybean yield" can also include pods per plant, pods per acre, seeds per plant, seeds per pod, weight per seed, weight per pod, pods per node, number of nodes, and the number of internodes per plant.

In still further embodiments, "sugarcane yield" can be measured as cane yield (tons per acre; kg/hectare), total recoverable sugar (pounds per ton), and sugar yield (tons/acre).

In yet still further embodiments, "wheat yield" can include: cereal per unit area, grain number, grain weight, grain size, grains per head, seeds per head, seeds per plant, heads per acre, number of viable tillers per plant, composition of seed (for example, carbohydrates, starch, oil, and protein) and characteristics of seed fill.

The terms "yield", "seed yield" are defined above for a number of core crops. The terms "increased", "improved", "enhanced" are interchangeable and are defined herein.

The present disclosure also provides a method for the production of plants having increased yield. Performance of the method gives plants having increased yield. "Increased yield" can manifest as one or more of the following: (i) increased plant biomass (weight) of one or more parts of a plant, particularly aboveground (harvestable) parts, of a plant, increased root biomass (increased number of roots, increased root thickness, increased root length) or increased biomass of any other harvestable part; (ii) increased early vigor, defined herein as an improved seedling aboveground area approximately three weeks post-germination. "Early vigor" refers to active healthy plant growth especially during early stages of plant growth, and can result from increased plant fitness due to, for example, the plants being better adapted to their environment (for example, optimizing the use of energy resources, uptake of nutrients and partitioning carbon allocation between shoot and root). Early vigor in corn, for example, is a combination of the ability of corn seeds to germinate and emerge after planting and the ability of the young corn plants to grow and develop after emergence. Plants having early vigor also show increased seedling survival and better establishment of the crop, which often results in highly uniform fields with the majority of the plants reaching the various stages of development at substantially the same time, which often results in increased yield. Therefore early vigor can be determined by measuring various factors, such as kernel weight, percentage germination, percentage emergence, seedling growth, seedling height, root length, root and shoot biomass, canopy size and color and others; (iii) increased total seed yield, which includes an increase in seed biomass (seed weight) and which can be an increase in the seed weight per plant or on an individual seed basis; increased number of panicles per plant; increased pods, increased number of nodes, increased number of flowers ("florets") per panicle/plant; increased seed fill rate; increased number of filled seeds; increased seed size (length, width, area, perimeter), which can also influence the composition of seeds; increased seed volume, which can also influence the composition of seeds. Increased yield can also result in modified architecture, or can occur because of modified plant architecture; (iv) increased harvest index, which is expressed as a ratio of the yield of harvestable parts, such as seeds, over the total biomass; and (v) increased kernel weight, which is extrapolated from the number of filled seeds counted and their total weight. An increased kernel weight can result from an increased seed size and/or seed weight, an increase in embryo size, endosperm size, aleurone and/or scutellum, or other parts of the seed.

In one embodiment, increased yield can be increased seed yield, and is selected from one of the following: (i) increased seed weight; (ii) increased number of filled seeds; and (iii) increased harvest index.

The disclosure also extends to harvestable parts of a plant such as, but not limited to, seeds, leaves, fruits, flowers, bolls, stems, rhizomes, tubers and bulbs. The disclosure furthermore relates to products derived from a harvestable part of such a plant, such as dry pellets, powders, oil, fat and fatty acids, starch or proteins.

The present disclosure provides a method for increasing "yield" of a plant or "broad acre yield" of a plant or plant part defined as the harvestable plant parts per unit area, for example seeds, or weight of seeds, per acre, pounds per acre, bushels per acre, tones per acre, tons per acre, kilo per hectare.

This disclosure further provides a method of increasing yield in a plant by producing a plant comprising a polynucleic acid sequence encoding a polypeptide of this disclosure where the plant can be crossed with itself, a second plant from the same plant line, a wild type plant, or a plant from a different line of plants to produce a seed. The seed of the resultant plant can be harvested from fertile plants and be used to grow progeny generations of plant(s) of this disclosure. In addition to direct transformation of a plant with a recombinant DNA, transgenic plants can be prepared by crossing a first plant having a recombinant DNA with a second plant lacking the DNA. For example, recombinant DNA can be introduced into a first plant line that is amenable to transformation to produce a transgenic plant which can be crossed with a second plant line to introgress the recombinant DNA into the second plant line. A transgenic plant with a recombinant DNA having the polynucleotide of this disclosure provides the enhanced trait of increased yield compared to a control plant. Genetic markers associated with recombinant DNA can produce transgenic progeny that is homozygous for the desired recombinant DNA. Progeny plants carrying DNA for both parental traits can be back crossed into a parent line multiple times, for example usually 6 to 8 generations, to produce a progeny plant with substantially the same genotype as the one original transgenic parental line but having the recombinant DNA of the other transgenic parental line. The term "progeny" denotes the offspring of any generation of a parent plant prepared by the methods of this disclosure containing the recombinant polynucleotides as described herein.

As used herein "nitrogen use efficiency" refers to the processes which lead to an increase in the plant's yield, biomass, vigor, and growth rate per nitrogen unit applied. The processes can include the uptake, assimilation, accumulation, signaling, sensing, retranslocation (within the plant) and use of nitrogen by the plant.

As used herein "nitrogen limiting conditions" refers to growth conditions or environments that provide less than optimal amounts of nitrogen needed for adequate or successful plant metabolism, growth, reproductive success and/or viability.

As used herein the "increased nitrogen stress tolerance" refers to the ability of plants to grow, develop, or yield normally, or grow, develop, or yield faster or better when subjected to less than optimal amounts of available/applied nitrogen, or under nitrogen limiting conditions.

As used herein "increased nitrogen use efficiency" refers to the ability of plants to grow, develop, or yield faster or better than normal when subjected to the same amount of available/applied nitrogen as under normal or standard conditions; ability of plants to grow, develop, or yield normally, or grow, develop, or yield faster or better when subjected to less than optimal amounts of available/applied nitrogen, or under nitrogen limiting conditions.

Increased plant nitrogen use efficiency can be translated in the field into either harvesting similar quantities of yield, while supplying less nitrogen, or increased yield gained by supplying optimal/sufficient amounts of nitrogen. The increased nitrogen use efficiency can improve plant nitrogen stress tolerance, and can also improve crop quality and biochemical constituents of the seed such as protein yield and oil yield. The terms "increased nitrogen use efficiency", "enhanced nitrogen use efficiency", and "nitrogen stress tolerance" are used inter-changeably in the present disclosure to refer to plants with improved productivity under nitrogen limiting conditions.

As used herein "water use efficiency" refers to the amount of carbon dioxide assimilated by leaves per unit of water vapor transpired. It constitutes one of the most important traits controlling plant productivity in dry environments. "Drought tolerance" refers to the degree to which a plant is adapted to arid or drought conditions. The physiological responses of plants to a deficit of water include leaf wilting, a reduction in leaf area, leaf abscission, and the stimulation of root growth by directing nutrients to the underground parts of the plants. Plants are more susceptible to drought during flowering and seed development (the reproductive stages), as plant's resources are deviated to support root growth. In addition, abscisic acid (ABA), a plant stress hormone, induces the closure of leaf stomata (microscopic pores involved in gas exchange), thereby reducing water loss through transpiration, and decreasing the rate of photosynthesis. These responses improve the water-use efficiency of the plant on the short term. The terms "increased water use efficiency", "enhanced water use efficiency", and "increased drought tolerance" are used inter-changeably in the present disclosure to refer to plants with improved productivity under water-limiting conditions.

As used herein "increased water use efficiency" refers to the ability of plants to grow, develop, or yield faster or better than normal when subjected to the same amount of available/applied water as under normal or standard conditions; ability of plants to grow, develop, or yield normally, or grow, develop, or yield faster or better when subjected to reduced amounts of available/applied water (water input) or under conditions of water stress or water deficit stress.

As used herein "increased drought tolerance" refers to the ability of plants to grow, develop, or yield normally, or grow, develop, or yield faster or better than normal when subjected to reduced amounts of available/applied water and/or under conditions of acute or chronic drought; ability of plants to grow, develop, or yield normally when subjected to reduced amounts of available/applied water (water input) or under conditions of water deficit stress or under conditions of acute or chronic drought.

As used herein "drought stress" refers to a period of dryness (acute or chronic/prolonged) that results in water deficit and subjects plants to stress and/or damage to plant tissues and/or negatively affects grain/crop yield; a period of dryness (acute or chronic/prolonged) that results in water deficit and/or higher temperatures and subjects plants to stress and/or damage to plant tissues and/or negatively affects grain/crop yield.

As used herein "water deficit" refers to the conditions or environments that provide less than optimal amounts of water needed for adequate/successful growth and development of plants.

As used herein "water stress" refers to the conditions or environments that provide improper (either less/insufficient or more/excessive) amounts of water than that needed for adequate/successful growth and development of plants/crops thereby subjecting the plants to stress and/or damage to plant tissues and/or negatively affecting grain/crop yield.

As used herein "water deficit stress" refers to the conditions or environments that provide less/insufficient amounts of water than that needed for adequate/successful growth and development of plants/crops thereby subjecting the plants to stress and/or damage to plant tissues and/or negatively affecting grain yield.

As used herein a "polynucleotide" is a nucleic acid molecule comprising a plurality of polymerized nucleotides. A polynucleotide may be referred to as a nucleic acid, oligonucleotide, nucleotide, or any fragment thereof. In many instances, a polynucleotide encodes a polypeptide (or protein) or a domain or fragment thereof. Additionally, a polynucleotide can comprise a promoter, an intron, an enhancer region, a polyadenylation site, a translation initiation site, 5' or 3' untranslated regions, a reporter gene, a selectable marker, a scorable marker, or the like. A polynucleotide can be single-stranded or double-stranded DNA or RNA. A polynucleotide optionally comprises modified bases or a modified backbone. A polynucleotide can be, for example, genomic DNA or RNA, a transcript (such as an mRNA), a cDNA, a PCR product, a cloned DNA, a synthetic DNA or RNA, or the like. A polynucleotide can be combined with carbohydrate(s), lipid(s), protein(s), or other materials to perform a particular activity such as transformation or form a composition such as a peptide nucleic acid (PNA). A polynucleotide can comprise a sequence in either sense or antisense orientations. "Oligonucleotide" is substantially equivalent to the terms amplimer, primer, oligomer, element, target, and probe and is preferably single-stranded.

As used herein a "recombinant polynucleotide" or "recombinant DNA" is a polynucleotide that is not in its native state, for example, a polynucleotide comprises a series of nucleotides (represented as a nucleotide sequence) not found in nature, or a polynucleotide is in a context other than that in which it is naturally found; for example, separated from polynucleotides with which it typically is in proximity in nature, or adjacent (or contiguous with) polynucleotides with which it typically is not in proximity. The "recombinant polynucleotide" or "recombinant DNA" refers to polynucleotide or DNA which has been genetically engineered and constructed outside of a cell including DNA containing naturally occurring DNA or cDNA or synthetic DNA. For example, the polynucleotide at issue can be cloned into a vector, or otherwise recombined with one or more additional nucleic acids.

As used herein a "polypeptide" comprises a plurality of consecutive polymerized amino acid residues for example, at least about 15 consecutive polymerized amino acid residues. In many instances, a polypeptide comprises a series of polymerized amino acid residues that is a transcriptional regulator or a domain or portion or fragment thereof. Additionally, the polypeptide can comprise: (i) a localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

As used herein "protein" refers to a series of amino acids, oligopeptide, peptide, polypeptide or portions thereof whether naturally occurring or synthetic.

Recombinant DNA constructs are assembled using methods known to persons of ordinary skill in the art and typically comprise a promoter operably linked to DNA, the expression of which provides the enhanced agronomic trait. Other construct components can include additional regulatory elements, such as 5' leaders and introns for enhancing transcription, 3' untranslated regions (such as polyadenylation signals and sites), and DNA for transit or targeting or signal peptides.

As used herein a "recombinant polypeptide" is a polypeptide produced by translation of a recombinant polynucleotide.

A "synthetic polypeptide" is a polypeptide created by consecutive polymerization of isolated amino acid residues using methods known in the art.

An "isolated polypeptide", whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, for example, alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, for example, by any of the various protein purification methods.

A "DNA construct" as used in the present disclosure comprises at least one expression cassette having a promoter operable in plant cells and a polynucleotide of the present disclosure encoding a protein or variant of a protein or fragment of a protein that is functionally defined to maintain activity in transgenic host cells including plant cells, plant parts, explants and plants. DNA constructs are made that contain various genetic elements necessary for the expression of noncoding and coding polynucleotides in plants. Promoters, leaders, enhancers, introns, transit or targeting or signal peptides, 3' transcriptional termination regions are genetic elements that can be operably linked in a DNA construct.

Percent identity describes the extent to which polynucleotides or protein segments are invariant in an alignment of sequences, for example nucleotide sequences or amino acid sequences. An alignment of sequences is created by manually aligning two sequences, for example, a stated sequence, as provided herein, as a reference, and another sequence, to produce the highest number of matching elements, for example, individual nucleotides or amino acids, while allowing for the introduction of gaps into either sequence. An "identity fraction" for a sequence aligned with a reference sequence is the number of matching elements, divided by the full length of the reference sequence, not including gaps introduced by the alignment process into the reference sequence. "Percent identity" ("% identity") as used herein is the identity fraction times 100.

As used herein, a "functional fragment" refers to a portion of a polypeptide provided herein which retains full or partial molecular, physiological or biochemical function of the full length polypeptide. A functional fragment often contains the domain(s), such as Pfam domains, identified in the polypeptide provided in the sequence listing.

As used herein, a "homolog" or "homologues" means a protein in a group of proteins that perform the same biological function, for example, proteins that belong to the same Pfam protein family and that provide a common enhanced trait in transgenic plants of this disclosure.

Homologs are expressed by homologous genes. With reference to homologous genes, homologs include orthologs, for example, genes expressed in different species that evolved from a common ancestral genes by speciation and encode proteins retain the same function, but do not include paralogs, for example, genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins, or their corresponding nucleotide sequences, have typically at least about 60% identity, in some instances at least about 70%, at least about 75%, at least about bout 80%, at least about 85%, at least about 90%, at least about bout 92%, at least about bout 94%, at least about bout 95%, at least about 96%, at least about 97%, at least about 98%, at least about 99%, and even at least about 99.5% identity over the full length of a protein or its corresponding nucleotide sequence identified as being associated with imparting an enhanced trait when expressed in plant cells. In one aspect of the disclosure homolog proteins have an amino acid sequences that have at least about 80%, at least about 85%, at least about 90%, at least about 92%, at least about 94%, at least about 95%, at least about 96%, at least about 97%, at least about 98%, at least about 99%, and at least about 99.5% identity to a consensus amino acid sequence of proteins and homologs that can be built from sequences disclosed herein.

Homologs are inferred from sequence similarity, by comparison of protein sequences, for example, manually or by use of a computer-based tool using well-known sequence comparison algorithms such as BLAST and FASTA. A sequence search and local alignment program, for example, BLAST, can be used to search query protein sequences of a base organism against a database of protein sequences of various organisms, to find similar sequences, and the summary Expectation value (E-value) can be used to measure the level of sequence similarity. Because a protein hit with the lowest E-value for a particular organism may not necessarily be an ortholog or be the only ortholog, a reciprocal query is used to filter hit sequences with significant E-values for ortholog identification. The reciprocal query entails search of the significant hits against a database of protein sequences of the base organism. A hit can be identified as an ortholog, when the reciprocal query's best hit is the query protein itself or a paralog of the query protein. With the reciprocal query process orthologs are further differentiated from paralogs among all the homologs, which allows for the inference of functional equivalence of genes. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of the well-known conservative amino acid substitutions, for example, valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native protein or polypeptide can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side 30 chains is cysteine and methionine. Naturally conservative amino acids substitution groups are: valine-leucine, valine-isoleucine, phenylalanine-tyrosine, lysine-arginine, alaninevaline, aspartic acid-glutamic acid, and asparagine-glutamine. A further aspect of the disclosure includes proteins that differ in one or more amino acids from those of a described protein sequence as the result of deletion or insertion of one or more amino acids in a native sequence.

In general, the term "variant" refers to molecules with some differences, generated synthetically or naturally, in their nucleotide or amino acid sequences as compared to a reference (native) polynucleotides or polypeptides, respectively. These differences include substitutions, insertions, deletions or any desired combinations of such changes in a native polynucleotide or amino acid sequence.

With regard to polynucleotide variants, differences between presently disclosed polynucleotides and polynucleotide variants are limited so that the nucleotide sequences of the former and the latter are similar overall and, in many regions, identical. Due to the degeneracy of the genetic code, differences between the former and the latter nucleotide sequences may be silent (for example, the amino acids encoded by the polynucleotide are the same, and the variant polynucleotide sequence encodes the same amino acid sequence as the presently disclosed polynucleotide). Variant nucleotide sequences can encode different amino acid sequences, in which case such nucleotide differences will result in amino acid substitutions, additions, deletions, insertions, truncations or fusions with respect to the similarly disclosed polynucleotide sequences. These variations can result in polynucleotide variants encoding polypeptides that share at least one functional characteristic. The degeneracy of the genetic code also dictates that many different variant polynucleotides can encode identical and/or substantially similar polypeptides.

As used herein "gene" or "gene sequence" refers to the partial or complete coding sequence of a gene, its complement, and its 5' and/or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter can be subjected to subsequent processing such as chemical modification or folding to obtain a functional protein or polypeptide. By way of example, a transcriptional regulator gene encodes a transcriptional regulator polypeptide, which can be functional or require processing to function as an initiator of transcription.

As used herein, the term "promoter" refers generally to a DNA molecule that is involved in recognition and binding of RNA polymerase II and other proteins (trans-acting transcription factors) to initiate transcription. A promoter can be initially isolated from the 5' untranslated region (5' UTR) of a genomic copy of a gene. Alternately, promoters can be synthetically produced or manipulated DNA molecules. Promoters can also be chimeric, that is a promoter produced through the fusion of two or more heterologous DNA molecules. Plant promoters include promoter DNA obtained from plants, plant viruses, fungi and bacteria such as *Agrobacterium* and *Bradyrhizobium* bacteria.

Promoters which initiate transcription in all or most tissues of the plant are referred to as "constitutive" promoters. Promoters which initiate transcription during certain periods or stages of development are referred to as "developmental" promoters. Promoters whose expression is enhanced in certain tissues of the plant relative to other plant tissues are referred to as "tissue enhanced" or "tissue preferred" promoters. Promoters which express within a specific tissue of the plant, with little or no expression in other plant tissues are referred to as "tissue specific" promoters. A promoter that expresses in a certain cell type of the plant, for example a microspore mother cell, is referred to as a "cell type specific" promoter. An "inducible" promoter is a promoter in which transcription is initiated in response to an environmental stimulus such as cold, drought or light; or other stimuli such as wounding or chemical application. Many physiological and biochemical processes in plants exhibit endogenous rhythms with a period of about 24 hours. A "diurnal promoter" is a promoter which exhibits altered expression profiles under the control of a circadian oscillator. Diurnal regulation is subject to environmental inputs such as light and temperature and coordination by the circadian clock.

Sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252, zein Z27 as disclosed by Russell et al. (1997) *Transgenic Res.* 6(2):157-166, globulin 1 as disclosed by Belanger et al (1991) *Genetics* 129:863-872, glutelin 1 as disclosed by Russell (1997) supra, and peroxiredoxin antioxidant (Peri) as disclosed by Stacy et al. (1996) *Plant Mol Biol.* 31(6):1205-1216.

As used herein, the term "leader" refers to a DNA molecule isolated from the untranslated 5' region (5' UTR) of a genomic copy of a gene and is defined generally as a nucleotide segment between the transcription start site (TSS) and the protein coding sequence start site. Alternately, leaders can be synthetically produced or manipulated DNA elements. A leader can be used as a 5' regulatory element for modulating expression of an operably linked transcribable polynucleotide molecule.

As used herein, the term "intron" refers to a DNA molecule that can be isolated or identified from the genomic copy of a gene and can be defined generally as a region spliced out during mRNA processing prior to translation. Alternately, an intron can be a synthetically produced or manipulated DNA element. An intron can contain enhancer elements that effect the transcription of operably linked genes. An intron can be used as a regulatory element for modulating expression of an operably linked transcribable polynucleotide molecule. A DNA construct can comprise an intron, and the intron may or may not be heterologous with respect to the transcribable polynucleotide molecule.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide. Unlike promoters, enhancer elements do not usually include a transcription start site (TSS) or TATA box or equivalent sequence. A promoter can naturally comprise one or more enhancer elements that affect the transcription of an operably linked polynucleotide. An isolated enhancer element can also be fused to a promoter to produce a chimeric promoter cis-element, which confers an aspect of the overall modulation of gene expression. A promoter or promoter fragment can comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element can function to bind transcription factors that regulate transcription. Some enhancer elements bind more than one transcription factor, and transcription factors can interact with different affinities with more than one enhancer domain.

Expression cassettes of this disclosure can include a "transit peptide" or "targeting peptide" or "signal peptide" molecule located either 5' or 3' to or within the gene(s). These terms generally refer to peptide molecules that when linked to a protein of interest directs the protein to a particular tissue, cell, subcellular location, or cell organelle. Examples include, but are not limited to, chloroplast transit peptides (CTPs), chloroplast targeting peptides, mitochondrial targeting peptides, nuclear targeting signals, nuclear exporting signals, vacuolar targeting peptides, vacuolar sorting peptides. For description of the use of chloroplast transit peptides see U.S. Pat. No. 5,188,642 and U.S. Pat. No. 5,728,925. For description of the transit peptide region of an *Arabidopsis* EPSPS gene in the present disclosure, see Klee, H. J. et al (*MGG* (1987) 210:437-442. Expression cassettes of this disclosure can also include an intron or introns. Expression cassettes of this disclosure can contain a DNA near the 3' end of the cassette that acts as a signal to terminate transcription from a heterologous nucleic acid and that directs polyadenylation of the resultant mRNA. These are commonly referred to as "3'-untranslated regions" or "3'-non-coding sequences" or "3'-UTRs". The "3' non-translated sequences" means DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation signal can be derived from a natural gene, from a variety of plant genes, or from T-DNA. An example of a polyadenylation sequence is the nopaline synthase 3' sequence (nos 3'; Fraley et al., *Proc. Natl. Acad. Sci. USA* 80: 4803-4807, 1983). The use of different 3' non-translated sequences is exemplified by Ingelbrecht et al., *Plant Cell* 1:671-680, 1989.

Expression cassettes of this disclosure can also contain one or more genes that encode selectable markers and confer resistance to a selective agent such as an antibiotic or a herbicide. A number of selectable marker genes are known in the art and can be used in the present disclosure: selectable marker genes conferring tolerance to antibiotics like kanamycin and paromomycin (nptII), hygromycin B (aph IV), spectinomycin (aadA), U.S. Patent Publication 2009/0138985A1 and gentamycin (aac3 and aacC4) or tolerance to herbicides like glyphosate (for example, 5-enolpyruvyl-shikimate-3-phosphate synthase (EPSPS), U.S. Pat. No. 5,627,061; U.S. Pat. No. 5,633,435; U.S. Pat. No. 6,040,497; U.S. Pat. No. 5,094,945), sulfonyl herbicides (for example, acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366; 4,761,373; 5,633,437; 6,613,963; 5,013,659; 5,141,870; 5,378,824; 5,605,011)), bialaphos or phosphinothricin or derivatives (e.g., phosphinothricin acetyltransferase (bar) tolerance to phosphinothricin or glufosinate (U.S. Pat. Nos. 5,646,024; 5,561,236; 5,276,268; 5,637,489; 5,273,894); dicamba (dicamba monooxygenase, Patent Application Publications US2003/0115626A1), or sethoxydim (modified acetyl-coenzyme A carboxylase for conferring tolerance to cyclohexanedione (sethoxydim)), and aryloxyphenoxypropionate (haloxyfop, U.S. Pat. No. 6,414,222).

Transformation vectors of this disclosure can contain one or more "expression cassettes", each comprising a native or non-native plant promoter operably linked to a polynucleotide sequence of interest, which is operably linked to a 3' UTR termination signal, for expression in an appropriate host cell. It also typically comprises sequences required for proper translation of the polynucleotide or transgene. As used herein, the term "transgene" refers to a polynucleotide molecule artificially incorporated into a host cell's genome. Such a transgene can be heterologous to the host cell. The term "transgenic plant" refers to a plant comprising such a transgene. The coding region usually codes for a protein of interest but can also code for a functional RNA of interest, for example an antisense RNA, a nontranslated RNA, in the sense or antisense direction, a microRNA, a noncoding RNA, or a synthetic RNA used in either suppression or over expression of target gene sequences. The expression cassette comprising the nucleotide sequence of interest can be chimeric, meaning that at least one of its components is heterologous with respect to at least one of its other components. As used herein the term "chimeric" refers to a DNA molecule that is created from two or more genetically diverse sources, for example a first molecule from one gene or organism and a second molecule from another gene or organism.

Recombinant DNA constructs in this disclosure generally include a 3' element that typically contains a polyadenylation signal and site. Known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication 2002/0192813 A1; and the pea (*Pisum sativum*) ribulose biphosphate carboxylase gene (rbs 3'), and 3' elements from the genes within the host plant.

As used herein "operably linked" means the association of two or more DNA fragments in a recombinant DNA construct so that the function of one, for example, protein-encoding DNA, is controlled by the other, for example, a promoter.

As used herein "expressed" means produced, for example, a protein is expressed in a plant cell when its cognate DNA is transcribed to mRNA that is translated to the protein. An "expressed" protein can also include its truncated version (for example, N-terminal truncated, C-terminal truncated or internal truncated) as long as the truncated version maintains the same or similar functionality as the full length version.

Transgenic plants can comprise a stack of one or more polynucleotides disclosed herein resulting in the production of multiple polypeptide sequences. Transgenic plants comprising stacks of polynucleotides can be obtained by either or both of traditional breeding methods or through genetic engineering methods. These methods include, but are not limited to, crossing individual transgenic lines each comprising a polynucleotide of interest, transforming a transgenic plant comprising a first gene disclosed herein with a second gene, and co-transformation of genes into a single plant cell. Co-transformation of genes can be carried out using single transformation vectors comprising multiple genes or genes carried separately on multiple vectors.

Transgenic plants comprising or derived from plant cells of this disclosure transformed with recombinant DNA can be further enhanced with stacked traits, for example, a crop plant having an enhanced trait resulting from expression of DNA disclosed herein in combination with herbicide and/or pest resistance traits. For example, genes of the current disclosure can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects, or improved quality traits such as improved nutritional value. Herbicides for which transgenic plant tolerance has been demonstrated and the method of the present disclosure can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication 2003/0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in US Patent Application Publication 2003/010609 A1 for imparting N-amino methyl phosphonic acid tolerance; polynucleotide molecules disclosed in U.S. Pat. No. 6,107,549 for impartinig pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 6,506,599; 5,986,175 and US Patent Application Publication 2003/0150017 A1.

Plant Cell Transformation Methods

Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice). *Agrobacterium*-mediated transformation methods are described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), US Patent Application Publication 2004/0087030 A1 (cotton), and US Patent Application Publication 2001/0042257 A1 (sugar beet), all of which are incorporated herein by reference in their entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores, pollen, sperm and egg cells. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

For transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this disclosure can be resistant is a agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to a selective agent, or plant cells that have been scored positive in a screening assay, may be cultured in vitro to regenerate plantlets. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and plant species. Plants can be pollinated using conventional plant breeding methods known to those of skill in the art to produce seeds, for example self-pollination is commonly used with transgenic corn. The regenerated transformed plant or its progeny seed or plants can be tested for expression of the recombinant DNA and selected for the presence of an enhanced agronomic trait.

Transgenic Plants and Seeds

Transgenic plants derived from transgenic plant cells having a transgenic nucleus of this disclosure are grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits that contribute to increased yield or other traits that provide increased plant value, including, for example, improved seed quality. Of particular interest are plants having increased water use efficiency or drought tolerance, enhanced high temperature or cold tolerance, increased yield, increased nitrogen use efficiency.

Table 1 provides a list of protein-encoding DNA ("genes") as recombinant DNA for production of transgenic plants with enhanced traits, the elements of Table 1 are described by reference to:

"PEP SEQ ID NO" which identifies an amino acid sequence.

"NUC SEQ ID NO" which identifies a DNA sequence.

"Gene ID" which refers to an arbitrary identifier.

"Protein Name" which is a common name for protein encoded by the recombinant DNA.

TABLE 1

| NUC SEQ ID NO | PEP SEQ ID NO | Gene ID | Protein Name |
|---|---|---|---|
| 1 | 2 | TRDXM1-1 | OsNAC6 protein. |
| 3 | 4 | TRDXM1-2 | WRKY transcription factor. |
| 5 | 6 | TRDXM1-3 | ERF-like protein |
| 7 | 8 | TRDXM1-4 | PREDICTED: E3 ubiquitin-protein ligase ATL6-like. |
| 9 | 10 | TRDXM1-5 | Putative bHLH transcription factor. |
| 11 | 12 | TRDXM1-6 | Putative zinc finger transcription factor |
| 13 | 14 | TRDXM1-7 | Putative DNA repair protein rhp54. |
| 15 | 16 | TRDXM1-8 | Transcription factor-like protein bZIP1. |
| 17 | 18 | TRDXM1-9 | Stress-induced transcription factor NAC1. |
| 19 | 20 | TRDXM1-10 | Zinc finger protein. |

Selection Methods for Transgenic Plants with Enhanced Traits

Within a population of transgenic plants each regenerated from a plant cell with recombinant DNA many plants that survive to fertile transgenic plants that produce seeds and progeny plants will not exhibit an enhanced agronomic trait. Selection from the population is necessary to identify one or more transgenic plants with an enhanced trait. Transgenic plants having enhanced traits are selected from populations of plants regenerated or derived from plant cells transformed as described herein by evaluating the plants in a variety of assays to detect an enhanced trait, for example, increased water use efficiency or drought tolerance, enhanced high temperature or cold tolerance, increased yield, increased nitrogen use efficiency, enhanced seed composition such as enhanced seed protein and enhanced seed oil. These assays can take many forms including, but not limited to, direct screening for the trait in a greenhouse or field trial or by screening for a surrogate trait. Such analyses can be directed to detecting changes in the chemical composition, biomass, physiological property, or morphology of the plant. Changes in chemical compositions such as nutritional composition of grain can be detected by analysis of the seed composition and content of protein, free amino acids, oil, free fatty acids, starch or tocopherols. Changes in chemical compositions can also be detected by analysis of contents in leaves, such as chlorophyll or carotenoid contents. Changes in biomass characteristics can be evaluated on greenhouse or field grown plants and can include plant height, stem diameter, root and shoot dry weights, canopy size; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant to appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green or deleyed senescence, stalk lodging, root lodging, plant health, barreness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates screening assays for corn traits using hybrid corn plants. The assays can be adapted for screening other plants such as canola, wheat, cotton and soybean either as hybrids or inbreds.

Transgenic corn plants having increased nitrogen use efficiency can be identified by screening transgenic plants in the field under the same and sufficient amount of nitrogen supply as compared to control plants, where such plants provide higher yield as compared to control plants. Transgenic corn plants having increased nitrogen use efficiency can also be identified by screening transgenic plants in the field under reduced amount of nitrogen supply as compared to control plants, where such plants provide the same or similar yield as compared to control plants.

Transgenic corn plants having increased yield are identified by screening using progenies of the transgenic plants over multiple locations for several years with plants grown under optimal production management practices and maximum weed and pest control. Selection methods can be applied in multiple and diverse geographic locations, for example up to 16 or more locations, over one or more planting seasons, for example at least two planting seasons, to statistically distinguish yield improvement from natural environmental effects.

Transgenic corn plants having increased water use efficiency or drought tolerance are identified by screening plants in an assay where water is withheld for a period to induce stress followed by watering to revive the plants. For example, a selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Transgenic cotton plants with increased yield and increased water use efficiency are identified by growing under variable water conditions. Specific conditions for cotton include growing a first set of transgenic and control plants under "wet" conditions, for example irrigated in the range of 85 to 100 percent of evapotranspiration to provide leaf water potential of −14 to −18 bars, and growing a second set of transgenic and control plants under "dry" conditions, for example irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Increased water use efficiency is indicated by increased yield, improved relative water content, enhanced leaf water potential, increased biomass, enhanced leaf extension rates, and improved fiber parameters.

Although the plant cells and methods of this disclosure can be applied to any plant cell, plant, seed or pollen, for example, any fruit, vegetable, grass, tree or ornamental plant, the various aspects of the disclosure are applied to corn, soybean, cotton, canola, rice, barley, oat, wheat, turf grass, alfalfa, sugar beet, sunflower, *quinoa* and sugar cane plants.

Example 1

Corn Transformation

This example illustrates transformation methods in producing a transgenic corn plant cell, seed, and plant having altered phenotypes as shown in Tables 3-5, or an enhanced trait, for example, increased water use efficiency or drought tolerance, increased yield, increased nitrogen use efficiency.

For *Agrobacterium*-mediated transformation of corn embryo cells corn plants were grown in the greenhouse and ears were harvested when the embryos were 1.5 to 2.0 mm in length. Ears were surface-sterilized by spraying or soaking the ears in 80% ethanol, followed by air drying. Immature embryos were isolated from individual kernels on surface-sterilized ears. Shortly after excision, immature maize embryos were inoculated with overnight grown *Agrobacterium* cells, and incubated at room temperature with *Agrobacterium* for 5-20 minutes. Inoculated immature embryos were then co-cultured with *Agrobacterium* for 1 to 3 days at 23° C. in the dark. Co-cultured embryos were transferred to selection media and cultured for approximately two weeks to allow embryogenic callus to develop. Embryogenic calli were transferred to culture medium containing glyphosate and subcultured at about two week intervals. Transformed plant cells were recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants individual transgenic calli resulting from transformation and selection were placed on media to initiate shoot and root development into plantlets. Plantlets were transferred to potting soil for initial growth in a growth chamber at 26° C. followed by a mist bench before transplanting to 5 inch pots where plants were grown to maturity. The regenerated plants were self-fertilized and seeds were harvested for use in one or more methods to select seeds, seedlings or progeny second generation transgenic plants (R2 plants) or hybrids, for example, by selecting transgenic plants exhibiting an enhanced trait as compared to a control plant.

The above process can be repeated to produce multiple events of transgenic corn plants from cells that were transformed with recombinant DNA from the genes identified in Table 1. Progeny transgenic plants and seeds of the transformed plants were screened for the presence and single copy of the inserted gene, and for increased water use efficiency, increased yield, increased nitrogen use efficiency, and altered phenotypes as shown in Tables 3-5. From each group of multiple events of transgenic plants with a specific recombinant DNA from Table 1 the event(s) that showed increased yield, increased water use efficiency, increased nitrogen use efficiency, and altered phenotypes was (were) identified.

Example 2

Soybean transformation

This example illustrates plant transformation in producing a transgenic soybean plant cell, plant, and seed having an enhanced trait, for example increased water use efficiency, increased yield, and increased nitrogen use efficiency.

For *Agrobacterium* mediated transformation, soybean seeds were imbibed overnight and the meristem explants excised. Soybean explants were mixed with induced *Agrobacterium* cells containing plasmid DNA with the gene of interest cassette and a plant selectable marker cassette no later than 14 hours from the time of initiation of seed imbibition, and wounded using sonication. Following wounding, explants were placed in co-culture for 2-5 days at which point they were transferred to selection media to allow selection and growth of transgenic shoots. Resistant shoots were harvested in approximately 6-8 weeks and placed into selective rooting media for 2-3 weeks. Shoots producing roots were transferred to the greenhouse and potted in soil. Shoots that remained healthy on selection, but did not produce roots were transferred to non-selective rooting media for an additional two weeks. Roots from any shoots that produced roots off selection were tested for expression of the plant selectable marker before they were transferred to the greenhouse and potted in soil.

The above process can be repeated to produce multiple events of transgenic soybean plants from cells that were transformed with recombinant DNA from the genes identified in Table 1. Progeny transgenic plants and seed of the transformed plant cells were screened for the presence and single copy of the inserted gene, and for increased water use efficiency, increased yield, and increased nitrogen use efficiency.

Example 3

Cotton transformation

This example illustrates plant transformation in producing a transgenic cotton plant cell, plant, and seed having an enhanced trait, for example increased water use efficiency, increased yield, and increased nitrogen use efficiency.

Transgenic cotton plants containing each recombinant DNA from the genes identified in Table 1 were obtained by transforming cotton cells using *Agrobacterium*-mediated transformation as described in U.S. Pat. Nos. 7,790,460 and 7,947,869.

Progeny transgenic plants and seed of the transformed plant cells were screened for the presence and single copy of the inserted gene, and for increased water use efficiency, increased yield and increased nitrogen use efficiency. From each group of multiple events of transgenic plants with a specific recombinant DNA from Table 1 the event(s) that showed increased yield, increased water use efficiency, and increased nitrogen use efficiency was (were) identified.

Example 4

Canola Transformation

This example illustrates plant transformation in producing the transgenic canola plants of this disclosure and the production and identification of transgenic seed for transgenic canola having increased water use efficiency, increased yield, and increased nitrogen use efficiency.

Tissues from in vitro grown canola seedlings were prepared and inoculated with overnight-grown *Agrobacterium* cells containing plasmid DNA with a gene of interest cassette and a plant selectable marker cassette. Following co-cultivation with *Agrobacterium*, the infected tissues were allowed to grow on selection to promote growth of transgenic shoots, followed by growth of roots from the transgenic shoots. The selected plantlets were then transferred to the greenhouse and potted in soil. Molecular characterizations were performed to confirm the presence of the gene of interest, and its expression in transgenic plants and progenies. Progeny transgenic plants were selected from a population of transgenic canola events under specified growing conditions and were compared with control canola plants.

The above process can be repeated to produce multiple events of transgenic canola plants from cells that were transformed with recombinant DNA from the genes identified in Table 1. Progeny transgenic plants and seed of the transformed plant cells were screened for the presence and single copy of the inserted gene, and for increased water use efficiency, increased yield, and increased nitrogen use efficiency. From each group of multiple events of transgenic plants with a specific recombinant DNA from Table 1 the event(s) that showed increased yield, increased water use efficiency, increased nitrogen use efficiency and altered phenotypes was (were) identified.

Example 5

Identification of Altered Phenotypes in Automated Greenhouse

This example illustrates screening and identification of transgenic plants for altered phenotypes in an automated greenhouse (AGH). The apparatus and the methods for automated phenotypic screening of plants are disclosed in US Patent Publication No. US20110135161 (filed on Nov. 10, 2010), which is incorporated by reference herein in its entirety.

Screening and Identification of Transgenic Corn Plants for Altered Phenotypes.

Corn plants were tested in 3 screens in AGH under different conditions including non-stress, nitrogen deficit and water deficit stress conditions. All screens began with a non-stress condition during day 0-5 germination phase, after which the plants were grown for 22 days under screen specific conditions as shown in Table 2.

Water deficit is defined as a specific Volumetric Water Content (V WC) that is lower than the VWC of non-stress plant. For example, a non-stressed plant might be maintained at 55% VWC and water-deficit assay might be defined around 30% VWC as shown in Table 2. Data were collected using visible light and hyperspectral imaging as well as direct measurement of pot weight and amount of water and nutrient applied to individual plants on a daily basis.

Eight parameters were measured for each screen. The visible light color imaging based measurements are: biomass, canopy area and plant height. Biomass (B) is defined as estimated shoot fresh weight (g) of the plant obtained from images acquired from multiple angles of view. Canopy Area (Can) is defined as area of leaf as seen in top-down image (mm²). Plant Height (H) refers to the distance from the top of the pot to the highest point of the plant derived from side image (mm). Anthocyanin score, chlorophyll score and water content score are hyperspectral imaging based parameters. Anthocyanin Score (An) is an estimate of anthocyanin in the leaf canopy obtained from a top-down hyperspectral image. Chlorophyll Score (Chl) is a measurement of chlorophyll in the leaf canopy obtained from a top-down hyperspectral image. Water Content Score (WC) is a measurement of water in the leaf canopy obtained from a top-down hyperspectral image. Water Use Efficiency (WUE) is derived from the grams of plant biomass per liter of water added. Water Applied (WA) is a direct measurement of water added to a pot (pot with no hole) during the course of an experiment.

These physiological screen runs were set up so that tested transgenic lines were compared to a control line. The collected data were analyzed against the control using % delta and certain p-value cutoff. Tables 3-5 are summaries of transgenic corn plants comprising the disclosed recombinant DNA molecules with altered phenotypes under non stress, nitrogen deficit, and water deficit conditions, respectively.

"+" denotes an increase in the tested parameter at p≤0.1; whereas "−" denotes a decrease in the tested parameter at p≤0.1. The numbers in parenthesis show penetrance of the altered phenotypes, where the denominators represent total number of transgenic events tested for a given parameter in a specific screen, and the numerators represent the number of events showing a particular altered phenotype. For example, 7 transgenic plants were screened for anthocyanin score in the non-stress screen for TRDXM1-18 and 2 of the 7 tested showed increased anthocyanin at p≤0.1.

TABLE 2

Description of the 3 screens for corn plants.

| Screen | Description | Germination phase (5 days) | Screen specific phase (22 days) |
|---|---|---|---|
| Non-stress | well watered sufficient nitrogen | 55% VWC water | 55% VWC 8 mM nitrogen |
| Water deficit | limited watered sufficient nitrogen | 55% VWC water | 30% VWC 8 mM nitrogen |
| Nitrogen deficit | well watered low nitrogen | 55% VWC water | 55% VWC 2 mM nitrogen |

TABLE 3

Summary of transgenic corn plants with altered phenotypes in AGH non-stress screens.

| | Non-Stress | | | | |
|---|---|---|---|---|---|
| Gene_ID | An | B | H | WA | WUE |
| TRDXM1-6 | +(2/5) | −(2/5) | | | −(2/5) |
| TRDXM1-7 | | | | −(2/7) | |
| TRDXM1-8 | +(2/7) | | +(2/7) | | |
| TRDXM1-9 | | | −(4/5) | −(2/5) | |

TABLE 4

Summary of transgenic corn plants with altered phenotypes in AGH nitrogen-deficit screens

| | Nitrogen Deficit | | | | | |
|---|---|---|---|---|---|---|
| Gene_ID | B | Can | Chl | H | WA | WUE |
| TRDXM1-3 (Construct-624) | −(4/5) | −(2/5) | −(2/5) | −(4/5) | −(2/5) | −(3/5) |
| TRDXM1-4 | | +(2/3) | +(2/3) | | | |
| TRDXM1-6 | +(5/5) | +(4/5) | +(5/5) | +(5/5) | +(5/5) | +(5/5) |
| TRDXM1-7 | +(2/7) | | +(3/5) | | | +(2/7) |
| TRDXM1-8 | | −(2/7) | | | | |
| TRDXM1-9 | | −(2/5) | | −(2/5) | −(4/5) | +(2/5) |

TABLE 5

Summary of transgenic corn plants with altered phenotypes in AGH water-deficit screens

| | Water Deficit | | | | |
|---|---|---|---|---|---|
| Gene_ID | An | Can | H | WA | WC |
| TRDXM1-3 (Construct-624) | | | | | +(2/5) |
| TRDXM1-4 | | | | +(2/3) | +(2/3) |
| TRDXM1-6 | +(2/4) | | | +(3/4) | +(2/4) |
| TRDXM1-7 | | +(2/7) | | | |
| TRDXM1-8 | | | +(3/7) | +(2/7) | |
| TRDXM1-9 | | +(2/5) | +(2/5) | +(3/5) | |

Example 6

Phenotypic Evaluation of Transgenic Plants for Enhanced Nitrogen Use Efficiency

Corn Nitrogen field efficacy trials were conducted to identify genes that can improve nitrogen use efficiency under nitrogen limiting conditions leading to increased yield performance as compared to non transgenic controls. A yield increase in corn can be manifested as one or more of the following: an increase in the number of ears per plant, an increase in the number of rows, number of kernels per row, kernel weight, thousand kernel weight, fresh or dry ear length/diameter/biomass (weight), increase in the seed filling rate (which is the number of filled seeds divided by the total number of seeds and multiplied by 100), among others. For the Nitrogen field trial results shown in Table 6, each field was planted under nitrogen limiting condition (60 lbs/acre) and the corn ear weight or yield was compared to control plants to measure the yield increases.

Table 6 provides a list of protein encoding DNA or polynucleotide sequences ("genes") for producing transgenic corn plant with increased nitrogen use efficiency as compared to a control plant. Polynucleotide sequences in constructs with at least one event showing significant yield or ear weight increase across multiple locations at p≤0.2 are included. The elements of Table 6 are described by reference to:

"SEQ ID NO: polynucleotide" which identifies a nucleotide sequence from SEQ ID NO: 5, 7, 13, and 17.

"SEQ ID NO: polypeptide" which identifies an amino acid sequence from SEQ ID NO: 6, 8, 14, and 18.

"Gene identifier" which refers to an arbitrary identifier.

"NUE results" refers to the sequence in a construct with at least one event showing significant yield increase at p≤0.2 across locations. The first number refers to the number of events with significant yield or ear weight increase, whereas the second number refers to the total number of events tested for each sequence in a construct.

TABLE 6

Recombinant DNA for increased nitrogen use efficiency in corn

| SEQ ID NO: polynucleotide | SEQ ID NO: polypeptide | Gene Identifier | Nitrogen field trial Results | | |
|---|---|---|---|---|---|
| 5 | 6 | TRDXM1-3 (Construct-624) | 0/5 (Year-1: fresh ear weight) | 2/8 (Year-2: yield) | 2/5 (Year-3: fresh ear weight) |
| 5 | 6 | TRDXM1-3 (Construct-595) | 1/5 (fresh ear weight) | | |
| 7 | 8 | TRDXM1-4 | 1/5 (yield) | | |
| 13 | 14 | TRDXM1-7 | 1/5 (yield) | | |
| 17 | 18 | TRDXM1-9 | 2/5 (Year-1: fresh ear weight) | 1/6 (Year-2: yield) | |

Example 7

Phenotypic Evaluation of Transgenic Plants for Increased Yield

This example illustrates selection and identification of transgenic plants for increased yield in both dicotyledonous and monocotyledonous plants with primary examples presented for corn and canola are presented in Table 7 and 8 respectively. Polynucleotide sequences in constructs with at least one event that resulted in significant yield increase across locations at p≤0.2 are included.

Selection of Transgenic Plants with Enhanced Agronomic Trait(s): Increased Yield.

Effective selection of increased and/or enhanced yielding transgenic plants uses hybrid progenies of the transgenic plants for corn, cotton, and canola, or inbred progenies of transgenic plants for soybean plants plant such as corn, cotton, canola, or inbred plant such as soy, canola and cotton over multiple locations with plants grown under optimal production management practices. An exemplary target for improved yield is a 2% to 10% increase in yield as compared to yield produced by plants grown from seed of a control plant. Selection methods can be applied in multiple and diverse geographic locations, for example up to 16 or more locations, over one or more planting seasons, for example at least two planting seasons, to statistically distinguish yield improvement from natural environmental effects.

Increased Yield in Corn

Table 7 provides a list of protein encoding DNA or polynucleotide sequences ("genes") in the production of transgenic corn plant with increased yield as compared to a control plant. The elements of Table 7 are described by reference to:

"SEQ ID NO: polynucleotide" which identifies a nucleotide sequence from SEQ ID NO: 3, 5, 7, 9, 11, 13, 15, 17, and 19.

"SEQ ID NO: polypeptide" which identifies an amino acid sequence from SEQ ID NO: 4, 6, 8, 10, 12, 14, 16, 18, and 20.

"Gene identifier" which refers to an arbitrary identifier.

"Broad acre yield results" refers to the sequence in a construct with at least one event showing significant yield increase at p≤0.2 across locations. The first number refers to the number of events with significant yield increase, whereas the second number refers to the total number of events tested for each sequence in a construct. As indicated in Table 7, gene TRDXM1-3 was tested in two constructs and significantly positive events were identified for both constructs.

TABLE 7

Recombinant DNA for increased nitrogen use efficiency in corn

| SEQ ID NO: polynucleotide | SEQ ID NO: polypeptide | Gene Identifier | Broad Acre Yield Results | | |
|---|---|---|---|---|---|
| 3 | 4 | TRDXM1-2 | 1/7 (Year-1) | 1/3 (Year-2) | |
| 5 | 6 | TRDXM1-3 (Construct-624) | 2/8 (Year-1) | 1/6 (Year-2) | |
| 5 | 6 | TRDXM1-3 (Construct-595) | 2/8 | | |
| 7 | 8 | TRDXM1-4 | 0/6 (Year-1) | 1/3 (Year-2) | 2/3 (Year-3) |
| 9 | 10 | TRDXM1-5 | 1/7 (Year-1) | 1/7 (Year-2) | |
| 11 | 12 | TRDXM1-6 | 1/8 | | |
| 13 | 14 | TRDXM1-7 | 2/7 (Year-1) | 4/6 (Year-2) | 1/6 (Year-3) |
| 15 | 16 | TRDXM1-8 | 4/8 | | |
| 17 | 18 | TRDXM1-9 | 1/8 | | |
| 19 | 20 | TRDXM1-10 | 1/8 | | |

Increased Yield in Canola

A yield increase in canola can be manifested as one or more of the following: an increase in pod number, number of pods per plant, number of pods per node, number of internodes, incidence of pod shatter, seeds per silique, seed weight per silique, improved seed, oil, or protein composition.

Table 8 provides a list of protein encoding DNA or polynucleotide sequences ("genes") in the production of transgenic canola plant with increased yield as compared to a control plant. The elements of Table 8 are described by reference to:

"SEQ ID NO: polynucleotide" identifies a nucleotide sequence from SEQ ID NO: 1.

"SEQ ID NO: polypeptide" identifies an amino acid sequence from SEQ ID NO: 2.

"Gene identifier" which refers to an arbitrary identifier.

"Broad acre yield results" refers to the sequence in a construct with at least one event showing significant yield increase at p≤0.2 across locations. The first number refers to the number of events with significant yield increase, whereas the second number refers to the total number of events tested for each sequence in a construct.

TABLE 8

Canola Yield

| SEQ ID NO: polynucleotide | SEQ ID NO: polypeptide | Gene Identifier | Broad Acre Yield Results |
|---|---|---|---|
| 1 | 2 | TRDXM1-1 | 1/8 |

Example 8

Homolog Identification

This example illustrates the identification of homologs of proteins encoded by the DNA identified in Table 1 which were used to provide transgenic seed and plants having enhanced agronomic traits. From the sequences of the homolog proteins, corresponding homologous DNA sequences can be identified for preparing additional transgenic seeds and plants with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided in Table 1 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided in Table 1 using NCBI "blastp" program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs with at least 95% identity over the 95% length of the polypeptide sequences provided in Table 1 are reported below in Table 9 with the SEQ ID NO of the original query sequence and the identified homologs.

TABLE 9

Protein sequences and their homologs

| Peptide SEQ ID NO: | Homolog SEQ ID NOs |
|---|---|
| 2 | 21, 22 |
| 4 | 23, 24, 25, 26 |
| 12 | 27 |
| 14 | 28 |
| 18 | 29 |

We claimed:

1. A method for producing a maize plant comprising:

introducing into a plurality of maize plant cells a recombinant DNA molecule comprising a heterologous polynucleotide encoding a polypeptide, wherein the nucleotide sequence of said heterologous polynucleotide is selected from the group consisting of:

a.) a nucleotide sequence with at least 90% identity to SEQ ID NO: 17;

b.) a nucleotide sequence encoding a protein with at least 90% identity to SEQ ID NO: 18; and c.) a nucleotide sequence encoding a protein with at least 90% identity to SEQ ID NO: 29;

growing a plurality of maize plants from said maize plant cells; and identifying from said plurality of maize plants a maize plant comprising an enhanced trait of increased nitrogen use efficiency as compared to a control plant lacking said recombinant DNA molecule.

2. A method for increasing or nitrogen use efficiency in a maize plant comprising:

crossing a maize plant comprising a recombinant DNA molecule comprising a heterologous polynucleotide encoding a polypeptide, wherein the nucleotide sequence of said heterologous polynucleotide is selected from the group consisting of:

a.) a nucleotide sequence with at least 90% identity to SEQ ID NO: 17;

b.) a nucleotide sequence encoding a protein with at least 90% identity to SEQ ID NO: 18; and c.) a nucleotide sequence encoding a protein with at least 90% identity to SEQ ID NO: 29;

with itself, a second plant from the same plant line, a wild type plant, or a second plant from a different line of plants to produce a seed;

growing said seed to produce a plurality of progeny maize plants; and identifying and selecting a progeny maize plant having said recombinant DNA molecule and further comprising or increased nitrogen use efficiency compared to a control plant lacking said recombinant DNA molecule.

3. The method of claim 2, wherein said progeny maize plant has at least one altered phenotype selected from the group consisting of anthocyanin, biomass, canopy area, chlorophyll score, plant height, water applied, water content and water use efficiency as compared to a control plant.

4. The method of claim 2, wherein said nucleotide sequence of said polynucleotide comprises at least 95% identity to SEQ ID NO: 17.

5. The method of claim 2, wherein said nucleotide sequence encodes a protein having at least 95% identity to SEQ ID NO: 18 or 29.

6. The method of claim 2, wherein said nucleotide sequence encodes a protein having 100% identity to SEQ ID NO: 18 or 29.

7. The method of claim 1, wherein said nucleotide sequence comprises 100% identity to SEQ ID NO: 17.

8. The method of claim 1, wherein said nucleotide sequence encodes a protein having the amino acid sequence of SEQ ID NO: 18 or 29.

9. The method of claim 1, wherein said method comprises subjecting said plurality of maize plants to an assay for selecting for increased nitrogen use efficiency as compared to a control plant lacking said recombinant DNA molecule.

10. The method of claim 2, wherein said method comprises subjecting said plurality of progeny maize plants to an assay for selecting for increased nitrogen use efficiency as compared to a control plant lacking said recombinant DNA molecule.

* * * * *

SEQUENCE LISTING

```
<160> NUMBER OF SEQ ID NOS: 29

<210> SEQ ID NO 1
<211> LENGTH: 912
<212> TYPE: DNA
<213> ORGANISM: Oryza sativa
<220> FEATURE:
<223> OTHER INFORMATION: Coding sequence of SEQ ID NO: 2.

<400> SEQUENCE: 1
atgagcggcg gtcaggacct gcagctgccg ccggggttcc ggttccaccc gacggacgag      60
gagctggtga tgcactacct ctgccgccgc tgcgccggcc tccccatcgc cgtccccatc     120
atcgccgaga tcgacctcta caagttcgat ccatggcagc ttccccggat ggcgctgtac     180
ggagagaagg agtggtactt cttctcccCg cgagaccgca agtacccgaa cgggtcgcgg     240
ccgaaccgcg ccgccgggtc ggggtactgg aaggcgaccg gcgccgacaa gccggtgggc     300
tcgccgaagc cggtggcgat caagaaggcc ctcgtcttct acgccggcaa ggcgcccaag     360
ggcgagaaga ccaactggat catgcacgag taccgcctcg ccgacgtcga ccgctccgcc     420
cgcaagaaga acagcctcag gttggatgat tgggtgctgt gccggattta caacaagaag     480
ggcgggctgg agaagccgcc ggccgcggcg gtggcggcgg cggggatggt gagcagcggc     540
ggcggcgtcc agaggaagcc gatggtgggg gtgaacgcgg cggtgagctc ccgccggag      600 cagaagccgg tggtggcggg gccggcgttc ccggacctgg cggcgtacta cgaccggccg     660
```

```
tcggactcga tgccgcggct gcacgccgac tcgagctgct cggagcaggt gctgtcgccg    720
gagttcgcgt gcgaggtgca gagccagccc aagatcagcg agtgggagcg caccttcgcc    780
accgtcgggc ccatcaaccc cgccgcctcc atcctcgacc ccgccggctc cggcggcctc    840
ggcggcctcg gcggcggcgg cagcgacccc ctcctccagg acatcctcat gtactggggc    900
aagccattct ag                                                        912
```

<210> SEQ ID NO 2
<211> LENGTH: 303
<212> TYPE: PRT
<213> ORGANISM: Oryza sativa
<220> FEATURE:
<223> OTHER INFORMATION: OsNAC6 protein [Oryza sativa].

<400> SEQUENCE: 2

```
Met Ser Gly Gly Gln Asp Leu Gln Leu Pro Pro Gly Phe Arg Phe His
1               5                   10                  15

Pro Thr Asp Glu Glu Leu Val Met His Tyr Leu Cys Arg Arg Cys Ala
                20                  25                  30

Gly Leu Pro Ile Ala Val Pro Ile Ile Ala Glu Ile Asp Leu Tyr Lys
            35                  40                  45

Phe Asp Pro Trp Gln Leu Pro Arg Met Ala Leu Tyr Gly Glu Lys Glu
        50                  55                  60

Trp Tyr Phe Phe Ser Pro Arg Asp Arg Lys Tyr Pro Asn Gly Ser Arg
65                  70                  75                  80

Pro Asn Arg Ala Ala Gly Ser Gly Tyr Trp Lys Ala Thr Gly Ala Asp
                85                  90                  95

Lys Pro Val Gly Ser Pro Lys Pro Val Ala Ile Lys Lys Ala Leu Val
            100                 105                 110

Phe Tyr Ala Gly Lys Ala Pro Lys Gly Glu Lys Thr Asn Trp Ile Met
        115                 120                 125

His Glu Tyr Arg Leu Ala Asp Val Asp Arg Ser Ala Arg Lys Lys Asn
    130                 135                 140

Ser Leu Arg Leu Asp Asp Trp Val Leu Cys Arg Ile Tyr Asn Lys Lys
145                 150                 155                 160

Gly Gly Leu Glu Lys Pro Pro Ala Ala Val Ala Ala Ala Gly Met
                165                 170                 175

Val Ser Ser Gly Gly Val Gln Arg Lys Pro Met Val Gly Val Asn
            180                 185                 190

Ala Ala Val Ser Ser Pro Pro Glu Gln Lys Pro Val Val Ala Gly Pro
        195                 200                 205

Ala Phe Pro Asp Leu Ala Ala Tyr Tyr Asp Arg Pro Ser Asp Ser Met
    210                 215                 220

Pro Arg Leu His Ala Asp Ser Ser Cys Ser Glu Gln Val Leu Ser Pro
225                 230                 235                 240

Glu Phe Ala Cys Glu Val Gln Ser Gln Pro Lys Ile Ser Glu Trp Glu
                245                 250                 255

Arg Thr Phe Ala Thr Val Gly Pro Ile Asn Pro Ala Ala Ser Ile Leu
            260                 265                 270

Asp Pro Ala Gly Ser Gly Gly Leu Gly Gly Leu Gly Gly Gly Ser
        275                 280                 285

Asp Pro Leu Leu Gln Asp Ile Leu Met Tyr Trp Gly Lys Pro Phe
    290                 295                 300
```

<210> SEQ ID NO 3
<211> LENGTH: 618
<212> TYPE: DNA
<213> ORGANISM: Zea mays
<220> FEATURE:
<223> OTHER INFORMATION: Coding sequence of SEQ ID NO: 4.

<400> SEQUENCE: 3

```
atggcgactt cgctgggact gaaccctgaa gatctcttca cttcgtactc gtcttcctac      60
tactcctcgc cgccgttcat gtccgactac gcggcgagct tcacgccggc ggccggggac     120
tccacggcct tctcctcgga gctcgacgac cttcaccact tcgactactc accggcgccg     180
atcgtcactg ctgccggagc cggggctggg ggcggcgatc gcaacgagaa gatgatgtgg     240
tgtgagggtg gtggtgacga gaagactc agaagcaacg gaaggatcgg gttcagaacg       300
aggtcagagg tggagatctt ggacgacgga ttcaagtgga ggaagtacgg gaagaaggcc     360
gtcaagaaca gcccaaatcc aaggaactac taccgctgct cgtcggaggg ctgcggcgtg     420
aagaagcggg tggagaggga ccgcgacgac ccccgctacg tcatcaccac ctacgacggc     480
gtccacaacc acgccagccc cggagccgct gctatcatcg tcccgtacgg cagcggcggc     540
ggcaatagcg gcttctacag cccgccgcac agcggctccc cgtcggccac ctcctactcg     600
ggctccctag tcttctag                                                   618
```

<210> SEQ ID NO 4
<211> LENGTH: 205
<212> TYPE: PRT
<213> ORGANISM: Zea mays
<220> FEATURE:
<223> OTHER INFORMATION: WRKY transcription factor [Zea mays].

<400> SEQUENCE: 4

```
Met Ala Thr Ser Leu Gly Leu Asn Pro Glu Asp Leu Phe Thr Ser Tyr
1               5                   10                  15

Ser Ser Ser Tyr Tyr Ser Ser Pro Pro Phe Met Ser Asp Tyr Ala Ala
            20                  25                  30

Ser Phe Thr Pro Ala Ala Gly Asp Ser Thr Ala Phe Ser Ser Glu Leu
        35                  40                  45

Asp Asp Leu His His Phe Asp Tyr Ser Pro Ala Pro Ile Val Thr Ala
    50                  55                  60

Ala Gly Ala Gly Ala Gly Gly Asp Arg Asn Glu Lys Met Met Trp
65                  70                  75                  80

Cys Glu Gly Gly Gly Asp Glu Arg Arg Leu Arg Ser Asn Gly Arg Ile
                85                  90                  95

Gly Phe Arg Thr Arg Ser Glu Val Glu Ile Leu Asp Asp Gly Phe Lys
            100                 105                 110

Trp Arg Lys Tyr Gly Lys Lys Ala Val Lys Asn Ser Pro Asn Pro Arg
        115                 120                 125

Asn Tyr Tyr Arg Cys Ser Ser Glu Gly Cys Gly Val Lys Lys Arg Val
    130                 135                 140

Glu Arg Asp Arg Asp Asp Pro Arg Tyr Val Ile Thr Thr Tyr Asp Gly
145                 150                 155                 160

Val His Asn His Ala Ser Pro Gly Ala Ala Ile Ile Val Pro Tyr
                165                 170                 175

Gly Ser Gly Gly Gly Asn Ser Gly Phe Tyr Ser Pro Pro His Ser Gly
            180                 185                 190

Ser Pro Ser Ala Thr Ser Tyr Ser Gly Ser Leu Val Phe
        195                 200                 205
```

<210> SEQ ID NO 5
<211> LENGTH: 585
<212> TYPE: DNA
<213> ORGANISM: Glycine max
<220> FEATURE:
<223> OTHER INFORMATION: Coding sequence of SEQ ID NO: 6.

<400> SEQUENCE: 5

```
atgtgtggcg gagcaatcat cgcagatttc atacctcggc agcgtccccg caccctcaca     60
gcctccgaac tctggcccaa gcgcagcgaa cctcaacctc aacctcctcc tcctccagtt    120
aagaggcaga ggaaaaacct ctacagaggg atcaggcagc ggccctgggg caaatgggcc    180
gcggagattc gcgatccacg taaaggagtt cgtgtctggc ttggcacctt caacaccgcc    240
gaagaagccg ccagagccta cgacaaagaa gcccgaaaaa tccgcggcaa gaaagccaaa    300
gtcaatttcc ccaacgagga cgaccctctg ccgcaatacg gatcttgcaa gagcctcaac    360
ttggagttcg gttacgatct caaccaaaca gggcttttcc cttcttctaa cgctgatgag    420
aattgcgggt cccacgtggc ttactccgtt acggaagcca acaacaaagt agagaagctt    480
tccgaggagc ttatggcgta cgagaattta atgaggtttt atcagattcc ggaaaacgtc    540
gttggggatt tgtgggcctt tcctgacacc tctccacctc tctag                    585
```

<210> SEQ ID NO 6
<211> LENGTH: 194
<212> TYPE: PRT
<213> ORGANISM: Glycine max
<220> FEATURE:
<223> OTHER INFORMATION: ERF-like protein.

<400> SEQUENCE: 6

```
Met Cys Gly Gly Ala Ile Ile Ala Asp Phe Ile Pro Arg Gln Arg Pro
1               5                   10                  15

Arg Thr Leu Thr Ala Ser Glu Leu Trp Pro Lys Arg Ser Glu Pro Gln
            20                  25                  30

Pro Gln Pro Pro Pro Pro Pro Val Lys Arg Gln Arg Lys Asn Leu Tyr
        35                  40                  45

Arg Gly Ile Arg Gln Arg Pro Trp Gly Lys Trp Ala Ala Glu Ile Arg
    50                  55                  60

Asp Pro Arg Lys Gly Val Arg Val Trp Leu Gly Thr Phe Asn Thr Ala
65                  70                  75                  80

Glu Glu Ala Ala Arg Ala Tyr Asp Lys Glu Ala Arg Lys Ile Arg Gly
                85                  90                  95

Lys Lys Ala Lys Val Asn Phe Pro Asn Glu Asp Asp Pro Leu Pro Gln
            100                 105                 110

Tyr Gly Ser Cys Lys Ser Leu Asn Leu Glu Phe Gly Tyr Asp Leu Asn
        115                 120                 125

Gln Thr Gly Leu Phe Pro Ser Ser Asn Ala Asp Glu Asn Cys Gly Ser
    130                 135                 140

His Val Ala Tyr Ser Val Thr Glu Ala Asn Asn Lys Val Glu Lys Leu
145                 150                 155                 160

Ser Glu Glu Leu Met Ala Tyr Glu Asn Leu Met Arg Phe Tyr Gln Ile
                165                 170                 175

Pro Glu Asn Val Val Gly Asp Leu Trp Ala Phe Pro Asp Thr Ser Pro
            180                 185                 190

Pro Leu
```

<210> SEQ ID NO 7
<211> LENGTH: 1101
<212> TYPE: DNA
<213> ORGANISM: Glycine max
<220> FEATURE:
<223> OTHER INFORMATION: Coding sequence of SEQ ID NO: 8.

<400> SEQUENCE: 7

| | | | | |
|---|---|---|---|---|
| atgaagacag tcctattcct ccttctggtg tcagcgttaa tccccatcgc cgtcgcgcag | 60 |
| cccaatgact tctccgacgc aaacctcaac gagttcaact cctccatagc cataatcata | 120 |
| atcatattag taatcgcgtt tttcctcatg gcctttttct ccatctacgt gcgccactgc | 180 |
| gctgattccc cttccaacac cgtcaggcct ctcaccaccg cacgctccag gagggccgcg | 240 |
| cgtggccttg accccgctct gattcaaaca ttccctatcc tcgaatactc cgttgttaag | 300 |
| atccacaaaa tcgaaaagag agctttggaa tgcgctgtgt gtttgtgcga gttcgaggac | 360 |
| accgaaacgc tgcgtttgct ccccaagtgc gaccacgttt ccaccccga gtgcatcgac | 420 |
| gagtggttga gctcccacac cacgtgcccc gtgtgccgcg ccaacctcct tcccaccgag | 480 |
| tccgaggatg ctattgctaa cgccaacgcc aacggtgttg ttccagttcc ggaaacgtta | 540 |
| acgcgagaca tcgaatccca aaacgacgcc gtgcaagccg cgccagagca gcagaacgcg | 600 |
| gaggctgacc cagttttacc cgaaccggaa gttgtttccc tggacaaaac gctaaaccgg | 660 |
| aaccgcacgc gagggtcgcg gtcgaaccgg ccgcggaggt ttcccaggtc acactcgacc | 720 |
| gggcactcgc tggtccaacc gggagaaaac actgaccggt tcactttaaa gttgcctttg | 780 |
| gaggtgagga agcaattaat aaaccgccaa ttacaacgtg cgagtagctt gatcgtgtta | 840 |
| ccgagggaag gtagttcgag acagggttac cgaaccgggg agaagggag tagtagagcc | 900 |
| aaaatctcga gcggctgga ccggagtttg aaatcggacc ggtggatttt ctcaatggct | 960 |
| gcgcccttt ttgcaagggc gttgtctatt agatcgccta gggttcgaaa caatgatgtt | 1020 |
| gaaggagcgg cgtcctcgtc gtctcccacc gcgcctatca tgccgccgac ggccgttgac | 1080 |
| tcggcaaggc ctccggttta a | 1101 |

<210> SEQ ID NO 8
<211> LENGTH: 366
<212> TYPE: PRT
<213> ORGANISM: Glycine max
<220> FEATURE:
<223> OTHER INFORMATION: PREDICTED: E3 ubiquitin-protein ligase ATL6-
      like [Glycine max].

<400> SEQUENCE: 8

Met Lys Thr Val Leu Phe Leu Leu Val Ser Ala Leu Ile Pro Ile
1               5                   10                  15

Ala Val Ala Gln Pro Asn Asp Phe Ser Asp Ala Asn Leu Asn Glu Phe
            20                  25                  30

Asn Ser Ser Ile Ala Ile Ile Ile Ile Leu Val Ile Ala Phe Phe
        35                  40                  45

Leu Met Ala Phe Phe Ser Ile Tyr Val Arg His Cys Ala Asp Ser Pro
    50                  55                  60

Ser Asn Thr Val Arg Pro Leu Thr Thr Ala Arg Ser Arg Arg Ala Ala
65                  70                  75                  80

Arg Gly Leu Asp Pro Ala Leu Ile Gln Thr Phe Pro Ile Leu Glu Tyr
                85                  90                  95

Ser Val Val Lys Ile His Lys Ile Gly Lys Glu Ala Leu Glu Cys Ala
            100                 105                 110

Val Cys Leu Cys Glu Phe Glu Asp Thr Glu Thr Leu Arg Leu Leu Pro
        115                 120                 125

Lys Cys Asp His Val Phe His Pro Glu Cys Ile Asp Glu Trp Leu Ser
130                 135                 140

Ser His Thr Thr Cys Pro Val Cys Arg Ala Asn Leu Leu Pro Thr Glu
145                 150                 155                 160

Ser Glu Asp Ala Ile Ala Asn Ala Asn Ala Asn Gly Val Val Pro Val
                165                 170                 175

Pro Glu Thr Leu Thr Arg Asp Ile Glu Ser Gln Asn Asp Ala Val Gln
            180                 185                 190

Ala Ala Pro Glu Gln Gln Asn Ala Glu Ala Asp Pro Val Leu Pro Glu
        195                 200                 205

Pro Glu Val Val Ser Leu Asp Lys Thr Leu Asn Arg Asn Arg Thr Arg
    210                 215                 220

Gly Ser Arg Ser Asn Arg Pro Arg Arg Phe Pro Arg Ser His Ser Thr
225                 230                 235                 240

Gly His Ser Leu Val Gln Pro Gly Glu Asn Thr Asp Arg Phe Thr Leu
                245                 250                 255

Lys Leu Pro Leu Glu Val Arg Lys Gln Leu Ile Asn Arg Gln Leu Gln
            260                 265                 270

Arg Ala Ser Ser Leu Ile Val Leu Pro Arg Glu Gly Ser Ser Arg Gln
        275                 280                 285

Gly Tyr Arg Thr Gly Gly Glu Gly Ser Ser Arg Ala Lys Ile Ser Arg
    290                 295                 300

Arg Leu Asp Arg Ser Leu Lys Ser Asp Arg Trp Ile Phe Ser Met Ala
305                 310                 315                 320

Ala Pro Phe Phe Ala Arg Ala Leu Ser Ile Arg Ser Pro Arg Val Arg
                325                 330                 335

Asn Asn Asp Val Glu Gly Ala Ala Ser Ser Ser Pro Thr Ala Pro
            340                 345                 350

Ile Met Pro Pro Thr Ala Val Asp Ser Ala Arg Pro Pro Val
        355                 360                 365

<210> SEQ ID NO 9
<211> LENGTH: 780
<212> TYPE: DNA
<213> ORGANISM: Arabidopsis thaliana
<220> FEATURE:
<223> OTHER INFORMATION: Coding sequence of SEQ ID NO: 10.

<400> SEQUENCE: 9
atgcaatcca ctcatataag cggcggaagt agcggtggtg gtggtggagg aggaggagag      60
gtgagtcgaa gtggattatc tcggatccgt tcagctccag ctacttggat tgaaacccta     120
ctcgaagaag atgaagaaga aggtttaaaa cctaaccttt gtttaacaga gctgcttact     180
ggtaataata actctggagg agtgataacg agtcgtgacg actcgttcga gttcctgagt     240
tctgttgagc aaggattgta taatcatcat caaggtggtg gctttcaccg tcagaatagt     300
tctccggctg attttcttag tgggtctggt tctgggactg atgggtattt ctctaatttt     360
ggtattccgg cgaattatga ctatttgtcg accaacgttg atatttctcc gactaaacgg     420
tctagagata tggaaacaca gttttcttct cagctgaaag aagagcaaat gagtggtggg     480
atatcaggaa tgatggatat gaacatggac aagattttg aggattcagt tccttgtagg     540
gttcgtgcta acgtggttg tgctactcat cctcgtagca ttgctgaacg ggtgagaaga     600

```
acgcgaataa gtgatcggat taggaggctg caagagcttg ttcctaacat ggataagcaa    660
accaacactg cagacatgtt ggaagaagct gtggagtatg tgaaggctct tcaaagccag    720
atccaggaat tgacagagca gcagaagaga tgcaaatgca aacctaaaga agaacaatag    780
```

<210> SEQ ID NO 10
<211> LENGTH: 259
<212> TYPE: PRT
<213> ORGANISM: Arabidopsis thaliana
<220> FEATURE:
<223> OTHER INFORMATION: Putative bHLH transcription factor [Arabidopsis thaliana].

<400> SEQUENCE: 10

```
Met Gln Ser Thr His Ile Ser Gly Gly Ser Gly Gly Gly Gly Gly
1               5                   10                  15

Gly Gly Gly Glu Val Ser Arg Ser Gly Leu Ser Arg Ile Arg Ser Ala
            20                  25                  30

Pro Ala Thr Trp Ile Glu Thr Leu Leu Glu Glu Asp Glu Glu Gly
        35                  40                  45

Leu Lys Pro Asn Leu Cys Leu Thr Glu Leu Leu Thr Gly Asn Asn Asn
    50                  55                  60

Ser Gly Gly Val Ile Thr Ser Arg Asp Asp Ser Phe Glu Phe Leu Ser
65                  70                  75                  80

Ser Val Glu Gln Gly Leu Tyr Asn His His Gln Gly Gly Gly Phe His
                85                  90                  95

Arg Gln Asn Ser Ser Pro Ala Asp Phe Leu Ser Gly Ser Gly Ser Gly
            100                 105                 110

Thr Asp Gly Tyr Phe Ser Asn Phe Gly Ile Pro Ala Asn Tyr Asp Tyr
        115                 120                 125

Leu Ser Thr Asn Val Asp Ile Ser Pro Thr Lys Arg Ser Arg Asp Met
    130                 135                 140

Glu Thr Gln Phe Ser Ser Gln Leu Lys Glu Glu Gln Met Ser Gly Gly
145                 150                 155                 160

Ile Ser Gly Met Met Asp Met Asn Met Asp Lys Ile Phe Glu Asp Ser
                165                 170                 175

Val Pro Cys Arg Val Arg Ala Lys Arg Gly Cys Ala Thr His Pro Arg
            180                 185                 190

Ser Ile Ala Glu Arg Val Arg Arg Thr Arg Ile Ser Asp Arg Ile Arg
        195                 200                 205

Arg Leu Gln Glu Leu Val Pro Asn Met Asp Lys Gln Thr Asn Thr Ala
    210                 215                 220

Asp Met Leu Glu Glu Ala Val Glu Tyr Val Lys Ala Leu Gln Ser Gln
225                 230                 235                 240

Ile Gln Glu Leu Thr Glu Gln Gln Lys Arg Cys Lys Cys Lys Pro Lys
                245                 250                 255

Glu Glu Gln
```

<210> SEQ ID NO 11
<211> LENGTH: 1185
<212> TYPE: DNA
<213> ORGANISM: Zea mays
<220> FEATURE:
<223> OTHER INFORMATION: Coding sequence of SEQ ID NO: 12.

<400> SEQUENCE: 11

```
atgatgatga tgatgggaga gagagcgcac gcgcctccgt ggcagcgctc gccggcggcc    60
```

```
agcggcgtca cggacgcgga cgacgcgtct ccgtacgccc tcctagcggc gctgcagcat    120
tacctgccgt cgaacgaggt ggcggcgtac gacgaagacg acgaggaggc ggccctggcg    180
gcggcgaccg ccgccgtcga cgcgtacgcc tgcgacgagt tccggatgta cgagttcaag    240
gtgcggcggt gctcgcgcgg gcggaaccac gactggacgg cctgccccta cgcgcacccg    300
ggggagaagg cccggcggcg cgaccccagg cggtaccact actccggcgc cgcgtgcccg    360
gacttccgca agggcgggtg caagcgcggc gacgcgtgcg agttcgcgca cggggtgttc    420
gagtgctggc tccacccgtc gcgctaccgg acgcagccct gcaaggacgg caccggctgc    480
cgccgccgcg tctgcttctt cgcgcacacg ccggaccagc tccgcgtgcc gccgccgcgg    540
cagtccagcc ctaggggcgc ggcggcggcg gcgtcgccgc tggccgagtc gtacgacggc    600
tcgccgctcc gccgccaggc gttcgagagc tacctcacca agagcggcat cgtgtcgtcg    660
ccgccgccga ccagcacgct cgtctcgccg ccgaggtcgc cgccgtcgga gtccccgcca    720
atgtcgccag acgccgccgc cgcgctccgc cgcggctcgt ggccgggcgt agggtcgccc    780
gtcaacgagg tcctcgcgtc gatgcgccag ctgcggctcg gcgcggctc gccgaggtcg    840
gcgccttccg gcgggtcgtt cttgggcgga ggctacccgt tcgggtcccc aaagtcaccg    900
gccgggctgt acagcctccc gtccacgcca accaggccgc cccgggtgac cgtgaccacc    960
gcctccggcg ccaccgtcct caccgtggaa cgcctcaacc tcggactcat cggggacgag   1020
gagccggtga tggagagggt cgagtccggg agagccctcc gcgagaaggt gttcgagcgg   1080
ctcagcaaag aagccgccgt tcccagcgac accgccgcat ccgccaacgt tgagggagcg   1140
gcccccgccc cggatgttgg atgggtctcc gacctcatca actag                   1185
```

<210> SEQ ID NO 12
<211> LENGTH: 394
<212> TYPE: PRT
<213> ORGANISM: Zea mays
<220> FEATURE:
<223> OTHER INFORMATION: Putative zinc finger transcription factor.

<400> SEQUENCE: 12

```
Met Met Met Met Met Gly Glu Arg Ala His Ala Pro Pro Trp Gln Arg
1               5                   10                  15

Ser Pro Ala Ala Ser Gly Val Thr Asp Ala Asp Asp Ala Ser Pro Tyr
            20                  25                  30

Ala Leu Leu Ala Ala Leu Gln His Tyr Leu Pro Ser Asn Glu Val Ala
        35                  40                  45

Ala Tyr Asp Glu Asp Asp Glu Glu Ala Ala Leu Ala Ala Ala Thr Ala
    50                  55                  60

Ala Val Asp Ala Tyr Ala Cys Asp Glu Phe Arg Met Tyr Glu Phe Lys
65                  70                  75                  80

Val Arg Arg Cys Ser Arg Gly Arg Asn His Asp Trp Thr Ala Cys Pro
                85                  90                  95

Tyr Ala His Pro Gly Glu Lys Ala Arg Arg Arg Asp Pro Arg Arg Tyr
            100                 105                 110

His Tyr Ser Gly Ala Ala Cys Pro Asp Phe Arg Lys Gly Gly Cys Lys
        115                 120                 125

Arg Gly Asp Ala Cys Glu Phe Ala His Gly Val Phe Glu Cys Trp Leu
    130                 135                 140

His Pro Ser Arg Tyr Arg Thr Gln Pro Cys Lys Asp Gly Thr Gly Cys
145                 150                 155                 160

Arg Arg Arg Val Cys Phe Phe Ala His Thr Pro Asp Gln Leu Arg Val
```

|  | | 165 | | | 170 | | | 175 | | |
| --- | --- | --- | --- | --- | --- | --- | --- | --- | --- | --- |

Pro Pro Pro Arg Gln Ser Ser Pro Arg Gly Ala Ala Ala Ala Ser
        180                  185                190

Pro Leu Ala Glu Ser Tyr Asp Gly Ser Pro Leu Arg Arg Gln Ala Phe
    195                  200                205

Glu Ser Tyr Leu Thr Lys Ser Gly Ile Val Ser Pro Pro Thr
    210                  215              220

Ser Thr Leu Val Ser Pro Arg Ser Pro Ser Glu Ser Pro Pro
225                230              235              240

Met Ser Pro Asp Ala Ala Ala Ala Leu Arg Arg Gly Ser Trp Pro Gly
        245                  250              255

Val Gly Ser Pro Val Asn Glu Val Leu Ala Ser Met Arg Gln Leu Arg
        260                  265              270

Leu Gly Gly Gly Ser Pro Arg Ser Ala Pro Ser Gly Gly Ser Phe Leu
        275                  280              285

Gly Gly Gly Tyr Pro Phe Gly Ser Pro Lys Ser Pro Ala Gly Leu Tyr
    290                  295              300

Ser Leu Pro Ser Thr Pro Thr Arg Pro Ser Pro Val Thr Val Thr Thr
305                310              315              320

Ala Ser Gly Ala Thr Val Leu Thr Val Glu Arg Leu Asn Leu Gly Leu
        325                  330              335

Ile Gly Asp Glu Glu Pro Val Met Glu Arg Val Glu Ser Gly Arg Ala
    340                  345              350

Leu Arg Glu Lys Val Phe Glu Arg Leu Ser Lys Glu Ala Ala Val Pro
        355                  360              365

Ser Asp Thr Ala Ala Ser Ala Asn Val Glu Gly Ala Ala Pro Ala Pro
    370                  375              380

Asp Val Gly Trp Val Ser Asp Leu Ile Asn
385                390

<210> SEQ ID NO 13
<211> LENGTH: 1677
<212> TYPE: DNA
<213> ORGANISM: Oryza sativa
<220> FEATURE:
<223> OTHER INFORMATION: Coding sequence of SEQ ID NO: 14.

<400> SEQUENCE: 13

| | | |
|---|---|---|
| atggataact caaatgtcag tacaggtggc tgtgtgatag cacacactcc tggatctggg | 60 |
| aaaacactgc tgcttatctc atttctggtg agttacatga agctcaccc aagaagccgg | 120 |
| ccattggtcc ttactccaaa agctgcaatt catacatgga agagagaatt tgagaaatgg | 180 |
| ggcatttcac ttcctttaca tgtgttccac catgctaaca gaagtggcaa gccgttgggg | 240 |
| gcaatggatt ctaaactgcg gtcgttatta ataatttttc acagaccaac ctggacaaat | 300 |
| atgcgcctta tggattcttt ggacaaacta ttcaagtggc atgcacatcc aagcgtcctc | 360 |
| ctcatgacat actcatcttt cttagggatg acgaaacaag actcaaaagt gcgaaaccga | 420 |
| taccgagaat ttatcgcaga ggtcctgatg aacaaccctg gactcttgat tcttgacgag | 480 |
| gggcacaacc caagaagcaa caagtccaag ttgaggaagc tgctgatgaa ggtgaagact | 540 |
| gagttcagaa tcctcttatc tggcacggcc ttccagaaca actttgaaga gtacttcaac | 600 |
| accctatgtt tggccagacc tcggtttatc ggtgatatca tgagtgaact agtgccagag | 660 |
| aggaaaagag aaacagttgg caggagagcc aaacatcaag aagcagtggc acgccgcgcc | 720 |
| tttgtggaga agtgggccga agattgag tctgacaaca acatatcag aagtgatggt | 780 |

```
atcagtttgc taaacaagct tactcgtgga ttcatagatt cattcgaggg agcgaagctg     840
atcaaccttc cagggataca tgtgtatacc gtgttcatga agcccacgga cattcaggag     900
gagatgctgg caaaggtaac aatgcccaag ctcgggtcgt cccggttccc tctagaggtt     960
gagctgctca tcacgattgg ctccatccat ccttggctca taaaaacgac gaaggccgtc    1020
agcaccttct tcagtccagc cgaagtgaag aaggttgaga ggtacaagcg agacttcgcg    1080
gcggggtgca aggccaaatt tgtgatcgat ctgctgcaca gtcgtcgtt cagaggggag     1140 agggtgctga tattctgcca acgtgtcc ccgatcacgt tcctggtgaa gctgatagag      1200
atggtgtttg ggtggcggct cggggaggag gtgctggtgc ttcagggtga tcaggagctg    1260
cctgtccggt ccgatgtgat ggacaagttc aacggcgaca gcgcggggaa gaggaaggtg    1320
ctgatcgcgt cgacaacggc atgcgcgag gggatcagct tgacaggcgc gtcgaggctg     1380
gtgatgctgg actcggagtg gaaccactcc aagacgaggc aggcgatcgc gcgggcgttc    1440
cggcgtgggc aggagaggac ggtgtacgtc tacctcctgg tggcatctgg gacatgggag    1500
gaggagaagt acaacagcaa caggaggaaa gcttggatgt ccaaaatggt gttcctggga    1560
cgctatgttg atgattcctc gcaaaaccgt gtcactgaca tcgatgatga ggtcttgaag    1620
gagcttgccg atgaagatca caccggcacc ttccatatga ttgtcaagca agactag      1677
```

<210> SEQ ID NO 14
<211> LENGTH: 558
<212> TYPE: PRT
<213> ORGANISM: Oryza sativa
<220> FEATURE:
<223> OTHER INFORMATION: putative DNA repair protein rhp54
    [Oryza sativa Japonica Group].

<400> SEQUENCE: 14

```
Met Asp Asn Ser Asn Val Ser Thr Gly Gly Cys Val Ile Ala His Thr
1               5                   10                  15

Pro Gly Ser Gly Lys Thr Leu Leu Ile Ser Phe Leu Val Ser Tyr
            20                  25                  30

Met Lys Ala His Pro Arg Ser Arg Pro Leu Val Leu Thr Pro Lys Ala
        35                  40                  45

Ala Ile His Thr Trp Lys Arg Glu Phe Glu Lys Trp Gly Ile Ser Leu
    50                  55                  60

Pro Leu His Val Phe His His Ala Asn Arg Ser Gly Lys Pro Leu Gly
65                  70                  75                  80

Ala Met Asp Ser Lys Leu Arg Ser Leu Leu Asn Asn Phe His Arg Pro
                85                  90                  95

Thr Trp Thr Asn Met Arg Leu Met Asp Ser Leu Asp Lys Leu Phe Lys
            100                 105                 110

Trp His Ala His Pro Ser Val Leu Leu Met Thr Tyr Ser Ser Phe Leu
        115                 120                 125

Gly Met Thr Lys Gln Asp Ser Lys Val Arg Asn Arg Tyr Arg Glu Phe
    130                 135                 140

Ile Ala Glu Val Leu Met Asn Asn Pro Gly Leu Leu Ile Leu Asp Glu
145                 150                 155                 160

Gly His Asn Pro Arg Ser Asn Lys Ser Lys Leu Arg Lys Leu Leu Met
                165                 170                 175

Lys Val Lys Thr Glu Phe Arg Ile Leu Leu Ser Gly Thr Ala Phe Gln
            180                 185                 190

Asn Asn Phe Glu Glu Tyr Phe Asn Thr Leu Cys Leu Ala Arg Pro Arg
```

```
            195                 200                 205
Phe Ile Gly Asp Ile Met Ser Glu Leu Val Pro Glu Arg Lys Arg Glu
210                 215                 220

Thr Val Gly Arg Arg Ala Lys His Gln Glu Ala Val Ala Arg Arg Ala
225                 230                 235                 240

Phe Val Glu Lys Val Gly Gln Lys Ile Glu Ser Asp Asn Lys His Ile
                245                 250                 255

Arg Ser Asp Gly Ile Ser Leu Leu Asn Lys Leu Thr Arg Gly Phe Ile
                260                 265                 270

Asp Ser Phe Glu Gly Ala Lys Leu Ile Asn Leu Pro Gly Ile His Val
            275                 280                 285

Tyr Thr Val Phe Met Lys Pro Thr Asp Ile Gln Glu Glu Met Leu Ala
            290                 295                 300

Lys Val Thr Met Pro Lys Leu Gly Ser Ser Arg Phe Pro Leu Glu Val
305                 310                 315                 320

Glu Leu Leu Ile Thr Ile Gly Ser Ile His Pro Trp Leu Ile Lys Thr
                325                 330                 335

Thr Lys Ala Val Ser Thr Phe Phe Ser Pro Ala Glu Val Lys Lys Val
                340                 345                 350

Glu Arg Tyr Lys Arg Asp Phe Ala Ala Gly Cys Lys Ala Lys Phe Val
            355                 360                 365

Ile Asp Leu Leu His Lys Ser Ser Phe Arg Gly Glu Arg Val Leu Ile
370                 375                 380

Phe Cys His Asn Val Ser Pro Ile Thr Phe Leu Val Lys Leu Ile Glu
385                 390                 395                 400

Met Val Phe Gly Trp Arg Leu Gly Glu Glu Val Leu Val Leu Gln Gly
                405                 410                 415

Asp Gln Glu Leu Pro Val Arg Ser Asp Val Met Asp Lys Phe Asn Gly
                420                 425                 430

Asp Ser Ala Gly Lys Arg Lys Val Leu Ile Ala Ser Thr Thr Ala Cys
            435                 440                 445

Ala Glu Gly Ile Ser Leu Thr Gly Ala Ser Arg Leu Val Met Leu Asp
450                 455                 460

Ser Glu Trp Asn His Ser Lys Thr Arg Gln Ala Ile Ala Arg Ala Phe
465                 470                 475                 480

Arg Arg Gly Gln Glu Arg Thr Val Tyr Val Tyr Leu Leu Val Ala Ser
                485                 490                 495

Gly Thr Trp Glu Glu Glu Lys Tyr Asn Ser Asn Arg Arg Lys Ala Trp
                500                 505                 510

Met Ser Lys Met Val Phe Leu Gly Arg Tyr Val Asp Asp Ser Ser Gln
            515                 520                 525

Asn Arg Val Thr Asp Ile Asp Asp Glu Val Leu Lys Glu Leu Ala Asp
            530                 535                 540

Glu Asp His Thr Gly Thr Phe His Met Ile Val Lys Gln Asp
545                 550                 555

<210> SEQ ID NO 15
<211> LENGTH: 438
<212> TYPE: DNA
<213> ORGANISM: Arabidopsis thaliana
<220> FEATURE:
<223> OTHER INFORMATION: Coding sequence of SEQ ID NO: 16.

<400> SEQUENCE: 15
atggcaaacg cagagaagac aagttcaggt tccgacatag atgagaagaa aagaaaacgc    60
```

```
aagttatcaa accgcgaatc tgcaaggagg tcgcgtttga agaaacagaa gttaatggaa      120
gacacgattc atgagatctc cagtcttgaa cgacgaatca aagagaacag tgagagatgt      180
cgagctgtaa aacagaggct tgactcggtc gaaacggaga acgcgggtct tagatcggag      240
aagatttggc tctcgagtta cgttagcgat ttagagaata tgattgctac gacgagttta      300
acgctgacgc agagtggtgg tggcgattgt gtcgacgatc agaacgcaaa cgcgggaata      360
gcggttggag attgtagacg tacaccgtgg aaattgagtt gtggttctct acaaccaatg      420
gcgtccttta agacatag                                                   438
```

```
<210> SEQ ID NO 16
<211> LENGTH: 145
<212> TYPE: PRT
<213> ORGANISM: Arabidopsis thaliana
<220> FEATURE:
<223> OTHER INFORMATION: Transcription factor-like protein bZIP1
      [Arabidopsis thaliana].

<400> SEQUENCE: 16

Met Ala Asn Ala Glu Lys Thr Ser Ser Gly Ser Asp Ile Asp Glu Lys
1               5                   10                  15

Lys Arg Lys Arg Lys Leu Ser Asn Arg Glu Ser Ala Arg Arg Ser Arg
            20                  25                  30

Leu Lys Lys Gln Lys Leu Met Glu Asp Thr Ile His Glu Ile Ser Ser
        35                  40                  45

Leu Glu Arg Arg Ile Lys Glu Asn Ser Glu Arg Cys Arg Ala Val Lys
    50                  55                  60

Gln Arg Leu Asp Ser Val Glu Thr Glu Asn Ala Gly Leu Arg Ser Glu
65                  70                  75                  80

Lys Ile Trp Leu Ser Ser Tyr Val Ser Asp Leu Glu Asn Met Ile Ala
                85                  90                  95

Thr Thr Ser Leu Thr Leu Thr Gln Ser Gly Gly Gly Asp Cys Val Asp
            100                 105                 110

Asp Gln Asn Ala Asn Ala Gly Ile Ala Val Gly Asp Cys Arg Arg Thr
        115                 120                 125

Pro Trp Lys Leu Ser Cys Gly Ser Leu Gln Pro Met Ala Ser Phe Lys
    130                 135                 140

Thr
145
```

```
<210> SEQ ID NO 17
<211> LENGTH: 945
<212> TYPE: DNA
<213> ORGANISM: Oryza sativa
<220> FEATURE:
<223> OTHER INFORMATION: Coding sequence of SEQ ID NO: 18.

<400> SEQUENCE: 17
atggggatga ggagggagag ggacgcggag gcggagctga acctgccgcc ggggttcagg       60
ttccacccca cggacgacga gctggtggag cactacctgt gcaggaaggc ggcggggcag      120
cgcctgccgg tgccgatcat cgccgaggtg gatctctaca gttcgacccc gtgggatctg      180
cccgagcgcg cgctgttcgg cgccagggag tggtacttct tcaccccgcg ggatcgcaag      240
tatcctaatg ggtcacgccc caaccgcgcc gccggcaacg ggtactggaa ggccaccggc      300
gccgacaagc ccgtcgcgcc gcgggggcgc acgcttggga tcaagaaggc gctcgtgttc      360
tacgccggca aggcgccgcg aggggtcaag actgattgga tcatgcatga gtaccggctc      420
```

```
gccgatgctg gccgcgccgc cgcgggcgcc aagaagggat ctctcaggtt ggatgattgg      480
gtgctgtgtc ggctgtacaa caagaagaac gagtgggaga gatgcagca ggggaaggag       540 gtgaaggagg aggcgtccga catggttacg tcgcagtcgc actcgcacac ccactcgtgg      600
ggcgagacgc gcacgccgga gtcggagatc gtggacaacg accccttccc ggagctggac      660
tcgttcccgg cgttccagcc tgcgccgccg ccggcgacgg cgatgatggt gcccaagaaa      720
gaatcgatgg acgacgccac cgcggccgcc gccgccgccg ccaccatccc caggaacaac      780
agcagcctgt tcgtggacct gagctacgac gatatccagg catgtacag cggcctcgac       840 atgctgccgc cgggcgacga cttctactcg tcgctcttcg cgtcgccgcg ggtgaagggg      900
acgacgccac gcgccggcgc cggcatgggc atggtcccgt tctag                     945
```

<210> SEQ ID NO 18
<211> LENGTH: 314
<212> TYPE: PRT
<213> ORGANISM: Oryza sativa
<220> FEATURE:
<223> OTHER INFORMATION: Stress-induced transcription factor NAC1
      [Oryza sativa Japonica Group].

<400> SEQUENCE: 18

```
Met Gly Met Arg Arg Glu Arg Asp Ala Glu Ala Glu Leu Asn Leu Pro
1               5                   10                  15

Pro Gly Phe Arg Phe His Pro Thr Asp Glu Leu Val Glu His Tyr
            20                  25                  30

Leu Cys Arg Lys Ala Ala Gly Gln Arg Leu Pro Val Pro Ile Ile Ala
            35                  40                  45

Glu Val Asp Leu Tyr Lys Phe Asp Pro Trp Asp Leu Pro Glu Arg Ala
        50                  55                  60

Leu Phe Gly Ala Arg Glu Trp Tyr Phe Phe Thr Pro Arg Asp Arg Lys
65                  70                  75                  80

Tyr Pro Asn Gly Ser Arg Pro Asn Arg Ala Ala Gly Asn Gly Tyr Trp
                85                  90                  95

Lys Ala Thr Gly Ala Asp Lys Pro Val Ala Pro Arg Gly Arg Thr Leu
            100                 105                 110

Gly Ile Lys Lys Ala Leu Val Phe Tyr Ala Gly Lys Ala Pro Arg Gly
            115                 120                 125

Val Lys Thr Asp Trp Ile Met His Glu Tyr Arg Leu Ala Asp Ala Gly
        130                 135                 140

Arg Ala Ala Gly Ala Lys Lys Gly Ser Leu Arg Leu Asp Asp Trp
145                 150                 155                 160

Val Leu Cys Arg Leu Tyr Asn Lys Lys Asn Glu Trp Glu Lys Met Gln
                165                 170                 175

Gln Gly Lys Glu Val Lys Glu Glu Ala Ser Asp Met Val Thr Ser Gln
            180                 185                 190

Ser His Ser His Thr His Ser Trp Gly Glu Thr Arg Thr Pro Glu Ser
            195                 200                 205

Glu Ile Val Asp Asn Asp Pro Phe Pro Glu Leu Asp Ser Phe Pro Ala
        210                 215                 220

Phe Gln Pro Ala Pro Pro Ala Thr Ala Met Met Val Pro Lys Lys
225                 230                 235                 240

Glu Ser Met Asp Asp Ala Thr Ala Ala Ala Ala Ala Ala Thr Ile
                245                 250                 255

Pro Arg Asn Asn Ser Ser Leu Phe Val Asp Leu Ser Tyr Asp Asp Ile
```

```
                260                 265                 270
Gln Gly Met Tyr Ser Gly Leu Asp Met Leu Pro Pro Gly Asp Asp Phe
                275                 280                 285

Tyr Ser Ser Leu Phe Ala Ser Pro Arg Val Lys Gly Thr Thr Pro Arg
                290                 295                 300

Ala Gly Ala Gly Met Gly Met Val Pro Phe
305                 310
```

<210> SEQ ID NO 19
<211> LENGTH: 594
<212> TYPE: DNA
<213> ORGANISM: Arabidopsis thaliana
<220> FEATURE:
<223> OTHER INFORMATION: Coding sequence of SEQ ID NO: 20.

<400> SEQUENCE: 19

```
atggcgactg aaacatcttc tttgaagctc ttcggtataa acctacttga aacgacgtcg    60
gttcaaaacc agtcatcgga accaagaccc ggatccggat caggatccga gtcacgtaag   120
tacgagtgtc aatactgttg tagagagttt gctaactctc aagctcttgg tggtcaccaa   180
aacgctcaca gaaagagcg tcagcttctt aaacgtgcac agatgttagc tactcgtggt    240
ttgccacgtc atcataattt tcaccctcat accaatccgc ttctctccgc cttcgcgccg   300
ctgcctcacc tcctctctca gccgcatcct ccgccgcata tgatgctctc tccttcttct   360
tcgagttcta agtggcttta cggtgaacac atgtcgtcac aaaacgccgt tgggtacttt   420
catggtggaa gggactttta cggaggtggc atggagtcta tggccggaga agtaaagact   480
catggtggtt ctttgccgga gatgaggagg ttcgccggag atagtgatcg gagtagcgga   540
attaagttag agaatggtat tgggctggac ctccatttaa gccttgggcc atag         594
```

<210> SEQ ID NO 20
<211> LENGTH: 197
<212> TYPE: PRT
<213> ORGANISM: Arabidopsis thaliana
<220> FEATURE:
<223> OTHER INFORMATION: Zinc finger protein [Arabidopsis thaliana].

<400> SEQUENCE: 20

```
Met Ala Thr Glu Thr Ser Ser Leu Lys Leu Phe Gly Ile Asn Leu Leu
1               5                   10                  15

Glu Thr Thr Ser Val Gln Asn Gln Ser Ser Glu Pro Arg Pro Gly Ser
                20                  25                  30

Gly Ser Gly Ser Glu Ser Arg Lys Tyr Glu Cys Gln Tyr Cys Cys Arg
            35                  40                  45

Glu Phe Ala Asn Ser Gln Ala Leu Gly Gly His Gln Asn Ala His Lys
        50                  55                  60

Lys Glu Arg Gln Leu Leu Lys Arg Ala Gln Met Leu Ala Thr Arg Gly
65                  70                  75                  80

Leu Pro Arg His His Asn Phe His Pro His Thr Asn Pro Leu Leu Ser
                85                  90                  95

Ala Phe Ala Pro Leu Pro His Leu Leu Ser Gln Pro His Pro Pro Pro
                100                 105                 110

His Met Met Leu Ser Pro Ser Ser Ser Ser Lys Trp Leu Tyr Gly
            115                 120                 125

Glu His Met Ser Ser Gln Asn Ala Val Gly Tyr Phe His Gly Gly Arg
        130                 135                 140

Gly Leu Tyr Gly Gly Gly Met Glu Ser Met Ala Gly Glu Val Lys Thr
```

His Gly Gly Ser Leu Pro Glu Met Arg Arg Phe Ala Gly Asp Ser Asp
145                 150                 155                 160

Arg Ser Ser Gly Ile Lys Leu Glu Asn Gly Ile Gly Leu Asp Leu His
            165                 170                 175

Leu Ser Leu Gly Pro
        180                 185                 190

Leu Ser Leu Gly Pro
    195

<210> SEQ ID NO 21
<211> LENGTH: 303
<212> TYPE: PRT
<213> ORGANISM: Oryza sativa
<220> FEATURE:
<223> OTHER INFORMATION: gi|125572883|gb|EAZ14398.1| hypothetical
      protein OsJ_04317 [Oryza sativa Japonica Group].

<400> SEQUENCE: 21

Met Ser Gly Gly Gln Asp Leu Gln Leu Pro Pro Gly Phe Arg Phe His
1               5                   10                  15

Pro Thr Asp Glu Glu Leu Val Met His Tyr Leu Cys Arg Arg Cys Ala
            20                  25                  30

Gly Leu Pro Ile Ala Val Pro Ile Ile Ala Glu Ile Asp Leu Tyr Lys
        35                  40                  45

Phe Asp Pro Trp Gln Leu Pro Arg Met Ala Leu Tyr Gly Glu Lys Glu
    50                  55                  60

Trp Tyr Phe Phe Ser Pro Arg Asp Arg Lys Tyr Pro Asn Gly Ser Arg
65                  70                  75                  80

Pro Asn Arg Ala Ala Gly Ser Gly Tyr Trp Lys Ala Thr Gly Ala Asp
                85                  90                  95

Lys Pro Val Gly Ser Pro Lys Pro Val Ala Ile Lys Lys Ala Leu Val
            100                 105                 110

Phe Tyr Ala Gly Lys Ala Pro Lys Gly Glu Lys Thr Asn Trp Ile Met
        115                 120                 125

His Glu Tyr Arg Leu Ala Asp Val Asp Arg Ser Ala Arg Lys Lys Asn
    130                 135                 140

Ser Leu Arg Leu Asp Asp Trp Val Leu Cys Arg Ile Tyr Asn Lys Lys
145                 150                 155                 160

Gly Gly Leu Glu Lys Pro Pro Ala Ala Ala Val Ala Ala Ala Gly Met
                165                 170                 175

Val Ser Ser Gly Gly Gly Val Gln Arg Lys Pro Met Val Gly Val Asn
            180                 185                 190

Ala Ala Val Ser Ser Pro Pro Glu Gln Lys Pro Val Val Ala Gly Pro
        195                 200                 205

Ala Phe Pro Asp Leu Ala Ala Tyr Tyr Asp Arg Pro Ser Asp Ser Met
    210                 215                 220

Pro Arg Leu His Ala Asp Ser Ser Cys Ser Glu Gln Val Leu Ser Pro
225                 230                 235                 240

Glu Phe Ala Cys Glu Val Gln Ser Gln Pro Lys Ile Ser Glu Trp Glu
                245                 250                 255

Arg Thr Phe Ala Thr Val Gly Pro Ile Asn Pro Ala Ala Ser Ile Leu
            260                 265                 270

Asp Pro Ala Gly Ser Gly Gly Leu Gly Gly Leu Gly Gly Gly Gly Arg
        275                 280                 285

Asp Pro Leu Leu Gln Glu Ile Leu Met Tyr Trp Gly Lys Pro Phe
    290                 295                 300

<210> SEQ ID NO 22
<211> LENGTH: 303
<212> TYPE: PRT
<213> ORGANISM: Oryza sativa
<220> FEATURE:
<223> OTHER INFORMATION: gi|125528621|gb|EAY76735.1| hypothetical
    protein OsI_04690 [Oryza sativa Indica Group].

<400> SEQUENCE: 22

Met Ser Gly Gly Gln Asp Leu Gln Leu Pro Gly Phe Arg Phe His
1               5                   10                  15

Pro Thr Asp Glu Glu Leu Val Met His Tyr Leu Cys Arg Arg Cys Ala
            20                  25                  30

Gly Leu Pro Ile Ala Val Pro Ile Ile Ala Glu Ile Asp Leu Tyr Lys
        35                  40                  45

Phe Asp Pro Trp Gln Leu Pro Arg Met Ala Leu Tyr Gly Glu Lys Glu
    50                  55                  60

Trp Tyr Phe Phe Ser Pro Arg Asp Arg Lys Tyr Pro Asn Gly Ser Arg
65                  70                  75                  80

Pro Asn Arg Ala Ala Gly Ser Gly Tyr Trp Lys Ala Thr Gly Ala Asp
                85                  90                  95

Lys Pro Val Gly Ser Pro Lys Pro Val Ala Ile Lys Lys Ala Leu Val
            100                 105                 110

Phe Tyr Ala Gly Lys Ala Pro Lys Gly Glu Lys Thr Asn Trp Ile Met
        115                 120                 125

His Glu Tyr Arg Leu Ala Asp Val Asp Arg Ser Ala Arg Lys Lys Asn
    130                 135                 140

Ser Leu Arg Leu Asp Asp Trp Val Leu Cys Arg Ile Tyr Asn Lys Lys
145                 150                 155                 160

Gly Gly Leu Glu Lys Pro Pro Ala Ala Ala Val Ala Ala Ala Gly Met
                165                 170                 175

Val Ser Asn Gly Gly Val Glu Arg Lys Pro Met Val Gly Val Asn
            180                 185                 190

Ala Ala Val Ser Ser Pro Pro Glu Gln Lys Pro Val Val Ala Gly Pro
        195                 200                 205

Ala Phe Pro Asp Leu Ala Ala Tyr Tyr Asp Arg Pro Ser Asp Ser Met
    210                 215                 220

Pro Arg Leu His Ala Asp Ser Ser Cys Ser Glu Gln Val Leu Ser Pro
225                 230                 235                 240

Glu Phe Ala Cys Glu Val Gln Ser Gln Pro Lys Ile Ser Glu Trp Glu
                245                 250                 255

Arg Thr Phe Ala Thr Val Gly Pro Ile Asn Pro Ala Ala Ser Ile Leu
            260                 265                 270

Asp Pro Ala Gly Ser Gly Gly Leu Gly Gly Leu Gly Gly Gly Ser
        275                 280                 285

Asp Pro Leu Leu Gln Asp Ile Leu Met Tyr Trp Gly Lys Pro Phe
    290                 295                 300

<210> SEQ ID NO 23
<211> LENGTH: 198
<212> TYPE: PRT
<213> ORGANISM: Arabidopsis thaliana

<400> SEQUENCE: 23

Met Ala Thr Ser Leu Gly Leu Asn Pro Glu Asp Leu Phe Thr Ser Tyr
1               5                   10                  15

Ser Ser Ser Tyr Tyr Ser Ser Pro Pro Phe Met Ser Asp Tyr Ala Ala
            20                  25                  30

Ser Phe Thr Pro Ala Ala Gly Asp Ser Thr Ala Phe Ser Ser Glu Leu
        35                  40                  45

Asp Asp Leu His His Phe Asp Tyr Ser Pro Ala Pro Ile Val Thr Ala
 50                  55                  60

Ala Gly Ala Gly Ala Gly Gly Asp Arg Asn Glu Lys Met Met Tyr
 65                  70                  75                  80

Arg Arg Leu Arg Ser Asn Gly Arg Ile Gly Phe Arg Thr Arg Ser Glu
                85                  90                  95

Val Glu Ile Leu Asp Asp Gly Phe Lys Trp Arg Lys Tyr Gly Lys Lys
            100                 105                 110

Ala Val Lys Asn Ser Pro Asn Pro Arg Asn Tyr Tyr Arg Cys Ser Ser
            115                 120                 125

Glu Gly Cys Gly Val Lys Lys Arg Val Glu Arg Asp Arg Asp Pro
130                 135                 140

Arg Tyr Val Ile Thr Thr Tyr Asp Gly Val His Asn His Ala Ser Pro
145                 150                 155                 160

Gly Ala Ala Ala Ile Ile Val Pro Tyr Gly Ser Gly Gly Asn Ser
                165                 170                 175

Gly Phe Tyr Ser Pro Pro His Ser Gly Ser Pro Ser Ala Thr Ser Tyr
            180                 185                 190

Ser Gly Ser Leu Ala Phe
            195

<210> SEQ ID NO 24
<211> LENGTH: 206
<212> TYPE: PRT
<213> ORGANISM: Arabidopsis thaliana

<400> SEQUENCE: 24

Met Ala Thr Ser Leu Gly Leu Asn Pro Glu Asp Leu Phe Thr Ser Tyr
1               5                   10                  15

Ser Ser Ser Tyr Tyr Ser Ser Pro Pro Phe Met Ser Asp Tyr Ala Thr
            20                  25                  30

Ser Phe Thr Pro Ala Ala Gly Asp Ser Thr Ala Phe Ser Ser Glu Leu
        35                  40                  45

Asp Asp Leu His His Phe Asp Tyr Ser Pro Ala Pro Ile Val Thr Ala
 50                  55                  60

Ala Gly Ala Gly Ala Gly Gly Asp Arg Asn Glu Lys Met Met Trp
 65                  70                  75                  80

Cys Glu Gly Gly Gly Asp Glu Arg Ser Leu Arg Ser Asn Gly Arg
                85                  90                  95

Ile Gly Phe Arg Thr Arg Ser Glu Val Glu Ile Leu Asp Asp Gly Phe
            100                 105                 110

Lys Trp Arg Lys Tyr Gly Lys Lys Ala Val Lys Asn Ser Pro Asn Pro
            115                 120                 125

Arg Asn Tyr Tyr Arg Cys Ser Ser Glu Gly Cys Gly Val Lys Lys Arg
130                 135                 140

Val Glu Arg Asp Arg Asp Pro Arg Tyr Val Ile Thr Thr Tyr Asp
145                 150                 155                 160

Gly Val His Asn His Ala Ser Pro Ala Ala Ala Ile Ile Val Pro
                165                 170                 175

Tyr Gly Ser Gly Gly Asn Ser Gly Phe Tyr Ser Pro Pro His Ser
            180                 185                 190

Gly Ser Pro Ser Ala Thr Ser Tyr Ser Gly Ser Leu Val Phe
            195                 200                 205

<210> SEQ ID NO 25
<211> LENGTH: 205
<212> TYPE: PRT
<213> ORGANISM: Arabidopsis thaliana

<400> SEQUENCE: 25

Met Ala Thr Ser Leu Gly Leu Asn Pro Glu Asp Leu Phe Thr Ser Tyr
1               5                   10                  15

Ser Ser Ser Tyr Tyr Ser Ser Pro Pro Phe Met Ser Asp Tyr Ala Ala
            20                  25                  30

Ser Phe Thr Pro Ala Gly Gly Asp Ser Thr Ala Phe Ser Ser Glu Leu
        35                  40                  45

Asp Asn Leu His His Phe Asp Tyr Ser Pro Ala Pro Ile Val Thr Ala
    50                  55                  60

Ala Gly Ala Gly Ala Gly Gly Asp Arg Asn Glu Lys Met Met Trp
65                  70                  75                  80

Cys Gln Gly Gly Gly Asp Glu Arg Arg Leu Arg Ser Asn Gly Arg Ile
                85                  90                  95

Gly Phe Arg Thr Arg Ser Gln Val Glu Ile Leu Asp Asp Gly Phe Lys
            100                 105                 110

Trp Arg Lys Tyr Gly Lys Lys Ala Val Lys Asn Ser Pro Asn Pro Arg
        115                 120                 125

Asn Tyr Tyr Arg Cys Ser Ser Glu Gly Cys Gly Val Lys Lys Arg Val
    130                 135                 140

Glu Arg Asp Arg Asp Asp Pro Arg Tyr Val Ile Thr Thr Tyr Asp Gly
145                 150                 155                 160

Val His Asn His Ala Ser Pro Ala Ala Ala Ala Ile Ile Val Pro Tyr
                165                 170                 175

Gly Asn Gly Gly Gly Asn Ser Gly Phe Tyr Ser Pro Pro His Ser Gly
            180                 185                 190

Ser Pro Ser Ala Thr Ser Tyr Ser Gly Ser Leu Val Phe
        195                 200                 205

<210> SEQ ID NO 26
<211> LENGTH: 205
<212> TYPE: PRT
<213> ORGANISM: Zea mays
<220> FEATURE:
<223> OTHER INFORMATION: gi|223950141|gb|ACN29154.1| unknown [Zea mays].

<400> SEQUENCE: 26

Met Ala Thr Ser Leu Gly Leu Asn Pro Glu Asp Leu Phe Thr Ser Tyr
1               5                   10                  15

Ser Ser Ser Tyr Tyr Ser Ser Pro Pro Phe Met Ser Asp Tyr Ala Ala
            20                  25                  30

Ser Phe Thr Pro Ala Ala Gly Asp Ser Thr Ala Phe Ser Ser Glu Leu
        35                  40                  45

Asp Asp Leu His His Phe Asp Tyr Ser Pro Ala Pro Ile Val Thr Ala
    50                  55                  60

Ala Gly Ala Gly Ala Gly Gly Asp Arg Asn Glu Lys Met Met Trp
65                  70                  75                  80

Cys Glu Gly Gly Gly Asp Glu Arg Arg Leu Arg Ser Asn Gly Arg Ile
                85                  90                  95

```
Gly Phe Arg Thr Arg Ser Glu Val Glu Ile Leu Asp Asp Gly Phe Lys
            100                 105                 110

Trp Arg Lys Tyr Gly Lys Lys Ala Val Lys Asn Ser Pro Asn Pro Arg
        115                 120                 125

Asn Tyr Tyr Arg Cys Ser Ser Glu Gly Cys Gly Val Lys Lys Arg Val
    130                 135                 140

Glu Arg Asp Arg Asp Asp Pro Arg Tyr Val Ile Thr Thr Tyr Asp Gly
145                 150                 155                 160

Val His Asn His Ala Ser Pro Gly Ala Ala Ala Ile Ile Val Pro Tyr
                165                 170                 175

Gly Ser Gly Gly Gly Asn Ser Gly Phe Tyr Ser Pro Pro His Ser Gly
            180                 185                 190

Ser Pro Ser Ala Thr Ser Tyr Ser Gly Ser Leu Ala Phe
        195                 200                 205

<210> SEQ ID NO 27
<211> LENGTH: 391
<212> TYPE: PRT
<213> ORGANISM: Zea mays
<220> FEATURE:
<223> OTHER INFORMATION: gi|226507354|ref|NP_001144558.1| hypothetical
      protein LOC100277562 [Zea mays].

<400> SEQUENCE: 27

Met Met Met Met Gly Glu Arg Ala His Ala Pro Pro Trp Gln His Ser
1               5                   10                  15

Pro Ala Ala Ser Gly Val Thr Asp Ala Asp Asp Ala Ser Pro Tyr Ala
                20                  25                  30

Leu Leu Ala Ala Leu Gln His Tyr Leu Pro Ser Asn Glu Val Ala Ala
            35                  40                  45

Phe Asp Glu Asp Glu Glu Ala Ala Leu Ala Ala Thr Ala Ala
        50                  55                  60

Val Asp Ala Tyr Ala Cys Asp Glu Phe Arg Met Tyr Glu Phe Lys Val
65                  70                  75                  80

Arg Arg Cys Ser Arg Gly Arg Asn His Asp Trp Thr Ala Cys Pro Tyr
                85                  90                  95

Ala His Pro Gly Glu Lys Ala Arg Arg Arg Asp Pro Arg Arg Tyr His
            100                 105                 110

Tyr Ser Gly Ala Ala Cys Pro Asp Phe Arg Lys Gly Gly Cys Lys Arg
        115                 120                 125

Gly Asp Ala Cys Glu Leu Ala His Gly Val Phe Glu Cys Trp Leu His
    130                 135                 140

Pro Ser Arg Tyr Arg Thr Gln Pro Cys Lys Asp Gly Thr Gly Cys Arg
145                 150                 155                 160

Arg Arg Val Cys Phe Phe Ala His Thr Pro Asp Gln Leu Arg Val Pro
                165                 170                 175

Pro Pro Arg Gln Ser Ser Pro Gly Ala Ala Ala Ser Pro Leu
            180                 185                 190

Ala Glu Ser Tyr Asp Gly Ser Pro Leu Arg Arg Gln Ala Phe Glu Ser
        195                 200                 205

Tyr Leu Thr Lys Ser Gly Ile Val Ser Ser Pro Thr Ser Thr Leu
    210                 215                 220

Val Ser Pro Arg Ser Pro Ser Glu Ser Pro Met Ser Pro
225                 230                 235                 240

Asp Ala Ala Ala Ala Leu Arg Arg Gly Ser Trp Pro Gly Val Gly Ser
                245                 250                 255
```

```
Pro Val Asn Glu Val Leu Ala Ser Met Arg Gln Leu Arg Leu Gly Gly
            260                 265                 270

Gly Ser Pro Arg Ser Ala Pro Ser Gly Gly Ser Phe Leu Gly Gly Gly
            275                 280                 285

Tyr Pro Phe Gly Ser Pro Lys Ser Pro Ala Gly Leu Tyr Ser Leu Pro
            290                 295                 300

Ser Thr Pro Thr Arg Pro Ser Pro Val Thr Val Thr Thr Ala Ser Gly
305                 310                 315                 320

Ala Thr Val Leu Thr Val Glu Arg Leu Asn Leu Gly Leu Ile Gly Asp
                325                 330                 335

Glu Glu Pro Val Met Glu Arg Val Glu Ser Gly Arg Ala Leu Arg Glu
            340                 345                 350

Lys Val Phe Glu Arg Leu Ser Lys Glu Ala Thr Val Pro Ser Asp Thr
            355                 360                 365

Ala Ala Ser Ala Asn Val Glu Gly Ala Ala Pro Ala Pro Asp Val Gly
            370                 375                 380

Trp Val Ser Asp Leu Ile Asn
385                 390

<210> SEQ ID NO 28
<211> LENGTH: 637
<212> TYPE: PRT
<213> ORGANISM: Oryza sativa
<220> FEATURE:
<223> OTHER INFORMATION: Putative DNA repair protein rhp54
      [Oryza sativa Japonica Group].

<400> SEQUENCE: 28

Met Gln Phe Asn Gly Asn Asp Tyr Lys Asp Arg Pro Gly Cys Ser Asn
1               5                   10                  15

Ile Cys Leu Asp Asp Asp Ile Leu Asp Pro Ser Leu Leu Ala Asn Leu
            20                  25                  30

Ala Pro Glu Leu Ser Glu Leu Lys Asn Ser Gly Ser Val Trp Ser Ala
            35                  40                  45

Ile Ser Asp Leu Asp Pro Lys Leu Leu Pro His Gln Arg Lys Ala Leu
50                  55                  60

Asp Phe Leu Trp Lys Asn Leu Ala Gly Ser Ile Gln Val Glu Gly Met
65                  70                  75                  80

Asp Asn Ser Asn Val Ser Thr Gly Gly Cys Val Ile Ala His Thr Pro
                85                  90                  95

Gly Ser Gly Lys Thr Leu Leu Leu Ile Ser Phe Leu Val Ser Tyr Met
            100                 105                 110

Lys Ala His Pro Arg Ser Arg Pro Leu Val Leu Thr Pro Lys Ala Ala
            115                 120                 125

Ile His Thr Trp Lys Arg Glu Phe Glu Lys Trp Gly Ile Ser Leu Pro
130                 135                 140

Leu His Val Phe His His Ala Asn Arg Ser Gly Lys Pro Leu Gly Ala
145                 150                 155                 160

Met Asp Ser Lys Leu Arg Ser Leu Leu Asn Asn Phe His Arg Pro Thr
            165                 170                 175

Trp Thr Asn Met Arg Leu Met Asp Ser Leu Asp Lys Leu Phe Lys Trp
            180                 185                 190

His Ala His Pro Ser Val Leu Leu Met Thr Tyr Ser Ser Phe Leu Gly
            195                 200                 205

Met Thr Lys Gln Asp Ser Lys Val Arg Asn Arg Tyr Arg Glu Phe Ile
```

```
                    210                 215                 220
Ala Glu Val Leu Met Asn Asn Pro Gly Leu Leu Ile Leu Asp Glu Gly
225                 230                 235                 240

His Asn Pro Arg Ser Asn Lys Ser Lys Leu Arg Lys Leu Leu Met Lys
                    245                 250                 255

Val Lys Thr Glu Phe Arg Ile Leu Leu Ser Gly Thr Ala Phe Gln Asn
                260                 265                 270

Asn Phe Glu Glu Tyr Phe Asn Thr Leu Cys Leu Ala Arg Pro Arg Phe
            275                 280                 285

Ile Gly Asp Ile Met Ser Glu Leu Val Pro Glu Arg Lys Arg Glu Thr
        290                 295                 300

Val Gly Arg Arg Ala Lys His Gln Glu Ala Val Ala Arg Arg Ala Phe
305                 310                 315                 320

Val Glu Lys Val Gly Gln Lys Ile Glu Ser Asp Asn Lys His Ile Arg
                325                 330                 335

Ser Asp Gly Ile Ser Leu Leu Asn Lys Leu Thr Arg Gly Phe Ile Asp
            340                 345                 350

Ser Phe Glu Gly Ala Lys Leu Ile Asn Leu Pro Gly Ile His Val Tyr
        355                 360                 365

Thr Val Phe Met Lys Pro Thr Asp Ile Gln Glu Met Leu Ala Lys
370                 375                 380

Val Thr Met Pro Lys Leu Gly Ser Ser Arg Phe Pro Leu Glu Val Glu
385                 390                 395                 400

Leu Leu Ile Thr Ile Gly Ser Ile His Pro Trp Leu Ile Lys Thr Thr
                405                 410                 415

Lys Ala Val Ser Thr Phe Phe Ser Pro Ala Glu Val Lys Lys Val Glu
            420                 425                 430

Arg Tyr Lys Arg Asp Phe Ala Ala Gly Cys Lys Ala Lys Phe Val Ile
        435                 440                 445

Asp Leu Leu His Lys Ser Ser Phe Arg Gly Glu Arg Val Leu Ile Phe
450                 455                 460

Cys His Asn Val Ser Pro Ile Thr Phe Leu Val Lys Leu Ile Glu Met
465                 470                 475                 480

Val Phe Gly Trp Arg Leu Gly Glu Glu Val Leu Val Leu Gln Gly Asp
                485                 490                 495

Gln Glu Leu Pro Val Arg Ser Asp Val Met Asp Lys Phe Asn Gly Asp
            500                 505                 510

Ser Ala Gly Lys Arg Lys Val Leu Ile Ala Ser Thr Thr Ala Cys Ala
        515                 520                 525

Glu Gly Ile Ser Leu Thr Gly Ala Ser Arg Leu Val Met Leu Asp Ser
530                 535                 540

Glu Trp Asn His Ser Lys Thr Arg Gln Ala Ile Ala Arg Ala Phe Arg
545                 550                 555                 560

Arg Gly Gln Glu Arg Thr Val Tyr Val Tyr Leu Leu Val Ala Ser Gly
                565                 570                 575

Thr Trp Glu Glu Glu Lys Tyr Asn Ser Asn Arg Arg Lys Ala Trp Met
            580                 585                 590

Ser Lys Met Val Phe Leu Gly Arg Tyr Val Asp Asp Ser Ser Gln Asn
        595                 600                 605

Arg Val Thr Asp Ile Asp Asp Glu Val Leu Lys Glu Leu Ala Asp Glu
610                 615                 620

Asp His Thr Gly Thr Phe His Met Ile Val Lys Gln Asp
625                 630                 635
```

```
<210> SEQ ID NO 29
<211> LENGTH: 315
<212> TYPE: PRT
<213> ORGANISM: Oryza sativa
<220> FEATURE:
<223> OTHER INFORMATION: Stress-induced transcription factor NAC1 [Oryza
      sativa Indica Group].

<400> SEQUENCE: 29

Met Gly Met Arg Arg Glu Arg Asp Ala Glu Ala Glu Leu Asn Leu Pro
1               5                   10                  15

Pro Gly Phe Arg Phe His Pro Thr Asp Asp Glu Leu Val Glu His Tyr
            20                  25                  30

Leu Cys Arg Lys Ala Ala Gly Gln Arg Leu Pro Val Pro Ile Ile Ala
        35                  40                  45

Glu Val Asp Leu Tyr Lys Phe Asp Pro Trp Asp Leu Pro Glu Arg Ala
    50                  55                  60

Phe Gly Ala Arg Glu Trp Tyr Phe Phe Thr Pro Arg Asp Arg Lys
65                  70                  75                  80

Tyr Pro Asn Gly Ser Arg Pro Asn Arg Ala Ala Gly Asn Gly Tyr Trp
                85                  90                  95

Lys Ala Thr Gly Ala Asp Lys Pro Val Ala Pro Arg Gly Arg Thr Leu
            100                 105                 110

Gly Ile Lys Lys Ala Leu Val Phe Tyr Ala Gly Lys Ala Pro Arg Gly
            115                 120                 125

Val Lys Thr Asp Trp Ile Met His Glu Tyr Arg Leu Ala Asp Ala Gly
130                 135                 140

Arg Ala Arg Pro Arg Ala Pro Arg Arg Asp Leu Ser Arg Leu Asp Asp
145                 150                 155                 160

Trp Val Leu Cys Arg Leu Tyr Asn Lys Lys Asn Glu Trp Glu Lys Met
                165                 170                 175

Gln Gln Gly Lys Glu Val Lys Glu Glu Ala Ser Asp Met Val Thr Ser
            180                 185                 190

Gln Ser His Ser His Thr His Ser Trp Gly Glu Thr Arg Thr Pro Glu
            195                 200                 205

Ser Glu Ile Val Asp Asn Asp Pro Phe Pro Glu Leu Asp Ser Phe Pro
    210                 215                 220

Ala Phe Gln Pro Ala Pro Pro Ala Thr Ala Met Met Val Pro Lys
225                 230                 235                 240

Lys Glu Ser Met Asp Asp Ala Thr Ala Ala Ala Ala Ala Ala Thr
                245                 250                 255

Ile Pro Arg Asn Asn Ser Ser Leu Phe Val Asp Leu Ser Tyr Asp Asp
                260                 265                 270

Ile Gln Gly Met Tyr Ser Gly Leu Asp Met Leu Pro Pro Gly Gly Asp
            275                 280                 285

Phe Tyr Ser Ser Leu Phe Ala Ser Pro Arg Val Lys Gly Thr Thr Pro
            290                 295                 300

Arg Ala Gly Ala Gly Met Gly Met Val Pro Phe
305                 310                 315
```